(12) United States Patent
Argento et al.

(10) Patent No.: US 12,290,456 B2
(45) Date of Patent: May 6, 2025

(54) PROSTHETIC CARDIAC VALVE DEVICES, SYSTEMS, AND METHODS

(71) Applicant: Shifamed Holdings, LLC, Campbell, CA (US)

(72) Inventors: Claudio Argento, Felton, CA (US); Andrew Backus, Santa Cruz, CA (US); Alice Yang, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/546,901

(22) Filed: Aug. 21, 2019

(65) Prior Publication Data

US 2020/0060852 A1     Feb. 27, 2020

Related U.S. Application Data

(60) Provisional application No. 62/720,853, filed on Aug. 21, 2018.

(51) Int. Cl.
*A61F 2/24*     (2006.01)
*A61F 2/88*     (2006.01)

(52) U.S. Cl.
CPC .............. *A61F 2/88* (2013.01); *A61F 2/2418* (2013.01); *A61F 2/2433* (2013.01);
(Continued)

(58) Field of Classification Search
CPC .................. A61F 2/2418; A61F 2/2427; A61F 2210/0014; A61F 2250/0039; A61F 2/2409; A61F 2/2433; A61F 2/2445; A61F 2210/0076; A61F 2220/0075; A61F 2/07; A61F 2/2442; A61F 2/915; A61F 2/958; A61F 2220/0008; A61F 2/24; A61F 2/243; A61F 2/88; A61F 2250/001;
(Continued)

(56) References Cited

U.S. PATENT DOCUMENTS

| 4,725,274 A | 2/1988 | Lane et al. |
| 5,002,563 A | 3/1991 | Pyka et al. |

(Continued)

FOREIGN PATENT DOCUMENTS

| AU | 2012261727 B2 | 10/2015 |
| AU | 2019246822 B2 | 8/2020 |

(Continued)

OTHER PUBLICATIONS

Westaby et al.; Adult human valve dimensions and their surgical significance; The American Journal of Cardiology; 53(4); pp. 552-556; Feb. 1984.

(Continued)

*Primary Examiner* — Ann Hu
(74) *Attorney, Agent, or Firm* — Shay Glenn LLP

(57) ABSTRACT

A heart valve prosthesis for replacing a diseased native valve in a patient. The valve prosthesis includes a compressible and expandable frame structure and an anchor connected to an outer periphery of the frame structure. The anchor comprises a helical wire having a free end. The valve may further include a valve segment mounted within the frame structure and expanded with the frame structure. The frame structure may be configured for receiving a valve segment.

20 Claims, 16 Drawing Sheets

(52) U.S. Cl.
CPC ............... *A61F 2220/0008* (2013.01); *A61F 2230/0004* (2013.01); *A61F 2230/0067* (2013.01); *A61F 2230/0091* (2013.01); *A61F 2250/001* (2013.01)

(58) Field of Classification Search
CPC ...... A61F 2230/0091; A61F 2230/0004; A61F 2230/0067; A61F 2002/825; A61F 2250/0063
See application file for complete search history.

(56) References Cited

U.S. PATENT DOCUMENTS

| | | | |
|---|---|---|---|
| 5,327,905 A | 7/1994 | Avitall | |
| 5,356,424 A | 10/1994 | Buzerak et al. | |
| 5,370,685 A | 12/1994 | Stevens | |
| 5,582,616 A | 12/1996 | Bolduc et al. | |
| 5,716,397 A | 2/1998 | Myers | |
| 5,755,601 A | 5/1998 | Jones | |
| 5,779,669 A | 7/1998 | Haissaguerre et al. | |
| 5,873,835 A | 2/1999 | Hastings et al. | |
| 5,944,690 A | 8/1999 | Falwell et al. | |
| 5,997,526 A | 12/1999 | Giba et al. | |
| 6,048,339 A | 4/2000 | Zirps et al. | |
| 6,053,873 A | 4/2000 | Govari et al. | |
| 6,254,550 B1 | 7/2001 | McNamara et al. | |
| 6,419,695 B1 | 7/2002 | Gabbay | |
| 6,419,696 B1 | 7/2002 | Ortiz et al. | |
| 6,530,952 B2 | 3/2003 | Vesely | |
| 6,533,783 B1 | 3/2003 | Töllner | |
| 6,641,553 B1 | 11/2003 | Chee et al. | |
| 6,752,813 B2 | 6/2004 | Goldfarb et al. | |
| 6,869,444 B2 | 3/2005 | Gabbay | |
| 6,908,478 B2 | 6/2005 | Alferness et al. | |
| 6,964,684 B2 | 11/2005 | Ortiz et al. | |
| 6,974,476 B2 | 12/2005 | McGuckin, Jr. et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,160,322 B2 | 1/2007 | Gabbay | |
| 7,175,656 B2 | 2/2007 | Khairkhahan | |
| 7,201,771 B2 | 4/2007 | Lane | |
| 7,226,467 B2 | 6/2007 | Lucatero et al. | |
| 7,381,219 B2 | 1/2008 | Salahieh et al. | |
| 7,329,279 B2 | 2/2008 | Haug et al. | |
| 7,445,631 B2 | 11/2008 | Salahieh et al. | |
| 7,470,285 B2 | 12/2008 | Nugent et al. | |
| 7,527,647 B2 | 5/2009 | Spence | |
| 7,534,261 B2 * | 5/2009 | Friedman ............... A61F 2/2409 623/2.18 | |
| 7,563,267 B2 | 7/2009 | Goldfarb et al. | |
| 7,594,903 B2 | 9/2009 | Webler et al. | |
| 7,604,646 B2 | 10/2009 | Goldfarb et al. | |
| 7,608,091 B2 | 10/2009 | Goldfarb et al. | |
| 7,618,449 B2 | 11/2009 | Tremulis et al. | |
| 7,621,948 B2 | 11/2009 | Herrmann et al. | |
| 7,666,204 B2 | 2/2010 | Thornton et al. | |
| 7,704,269 B2 | 4/2010 | St. Goar et al. | |
| 7,731,705 B2 | 6/2010 | Wardle | |
| 7,748,389 B2 | 7/2010 | Salahieh et al. | |
| 7,749,266 B2 | 7/2010 | Forster et al. | |
| 7,780,725 B2 | 8/2010 | Haug et al. | |
| 7,799,069 B2 | 9/2010 | Bailey et al. | |
| 7,811,296 B2 | 10/2010 | Goldfarb et al. | |
| 7,824,442 B2 | 11/2010 | Salahieh et al. | |
| 7,824,443 B2 | 11/2010 | Salahieh et al. | |
| 7,846,203 B2 | 12/2010 | Cribier | |
| 7,942,927 B2 | 5/2011 | Kaye et al. | |
| 7,947,075 B2 | 5/2011 | Goetz et al. | |
| 7,951,195 B2 | 5/2011 | Antonsson et al. | |
| 7,959,666 B2 | 6/2011 | Salahieh et al. | |
| 7,988,724 B2 | 8/2011 | Salahieh et al. | |
| 8,021,421 B2 | 9/2011 | Fogarty et al. | |
| 8,052,749 B2 | 11/2011 | Salahieh et al. | |
| 8,052,750 B2 | 11/2011 | Tuval et al. | |
| 8,062,355 B2 | 11/2011 | Figulla et al. | |
| 8,070,800 B2 | 12/2011 | Lock et al. | |
| 8,075,615 B2 | 12/2011 | Eberhardt et al. | |
| 8,096,985 B2 | 1/2012 | Legaspi et al. | |
| 8,147,541 B2 | 4/2012 | Forster et al. | |
| 8,147,542 B2 | 4/2012 | Maisano et al. | |
| 8,182,528 B2 | 5/2012 | Salahieh et al. | |
| 8,216,256 B2 | 7/2012 | Raschdorf et al. | |
| 8,236,049 B2 | 8/2012 | Rowe et al. | |
| 8,241,351 B2 | 8/2012 | Cabiri | |
| 8,251,977 B2 | 8/2012 | Partlett | |
| 8,252,050 B2 | 8/2012 | Maisano et al. | |
| 8,287,584 B2 | 10/2012 | Salahieh et al. | |
| 8,313,526 B2 | 11/2012 | Hoffman et al. | |
| 8,323,241 B2 | 12/2012 | Salahieh et al. | |
| 8,323,336 B2 | 12/2012 | Hill et al. | |
| 8,328,868 B2 | 12/2012 | Paul et al. | |
| 8,343,213 B2 | 1/2013 | Salahieh et al. | |
| 8,348,995 B2 | 1/2013 | Tuval et al. | |
| 8,348,996 B2 | 1/2013 | Tuval et al. | |
| 8,366,767 B2 | 2/2013 | Zhang | |
| 8,403,981 B2 | 3/2013 | Forster et al. | |
| 8,403,983 B2 | 3/2013 | Quadri et al. | |
| 8,414,643 B2 | 4/2013 | Tuval et al. | |
| 8,414,644 B2 | 4/2013 | Quadri et al. | |
| 8,414,645 B2 | 4/2013 | Dwork et al. | |
| 8,425,593 B2 | 4/2013 | Braido et al. | |
| 8,449,599 B2 | 5/2013 | Chau et al. | |
| 8,454,686 B2 | 6/2013 | Alkhatib | |
| 8,465,541 B2 | 6/2013 | Dwork | |
| 8,500,800 B2 | 8/2013 | Maisano et al. | |
| 8,512,401 B2 | 8/2013 | Murray et al. | |
| 8,523,881 B2 | 9/2013 | Cabiri et al. | |
| 8,545,553 B2 | 10/2013 | Zipory et al. | |
| 8,556,963 B2 | 10/2013 | Tremulis et al. | |
| 8,562,645 B2 | 10/2013 | Stone et al. | |
| 8,562,673 B2 | 10/2013 | Yeung et al. | |
| 8,579,962 B2 | 11/2013 | Salahieh et al. | |
| 8,603,157 B2 | 12/2013 | Seguin et al. | |
| 8,603,160 B2 | 12/2013 | Salahieh et al. | |
| 8,623,075 B2 | 1/2014 | Murray et al. | |
| 8,628,570 B2 | 1/2014 | Seguin | |
| 8,641,727 B2 | 2/2014 | Starksen et al. | |
| 8,652,202 B2 | 2/2014 | Alon et al. | |
| 8,652,203 B2 | 2/2014 | Quadri et al. | |
| 8,657,872 B2 * | 2/2014 | Seguin ............... A61F 2/2436 623/2.38 | |
| 8,685,086 B2 * | 4/2014 | Navia ............... A61F 2/2418 623/2.14 | |
| 8,696,693 B2 | 4/2014 | Najafi et al. | |
| 8,715,300 B2 | 5/2014 | Najafi et al. | |
| 8,715,342 B2 | 5/2014 | Zipory et al. | |
| 8,740,976 B2 | 6/2014 | Tran et al. | |
| 8,784,479 B2 | 7/2014 | Antonsson et al. | |
| 8,790,367 B2 | 7/2014 | Nguyen et al. | |
| 8,808,368 B2 | 8/2014 | Maisano et al. | |
| 8,828,078 B2 | 9/2014 | Salahieh et al. | |
| 8,834,564 B2 | 9/2014 | Tuval et al. | |
| 8,840,663 B2 | 9/2014 | Salahieh et al. | |
| 8,840,664 B2 | 9/2014 | Karapetian et al. | |
| 8,845,588 B2 | 9/2014 | Bruszewski | |
| 8,852,271 B2 | 10/2014 | Murray et al. | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,900,294 B2 | 12/2014 | Paniagua et al. | |
| 8,911,494 B2 | 12/2014 | Hammer et al. | |
| 8,920,369 B2 | 12/2014 | Salahieh et al. | |
| 8,926,690 B2 | 1/2015 | Kowalsky | |
| 8,926,696 B2 | 1/2015 | Cabiri et al. | |
| 8,926,697 B2 | 1/2015 | Gross et al. | |
| 8,940,002 B2 | 1/2015 | Goertzen | |
| 8,940,044 B2 | 1/2015 | Hammer et al. | |
| 8,951,299 B2 | 2/2015 | Paul et al. | |
| 8,986,371 B2 | 3/2015 | Quill et al. | |
| 8,998,980 B2 | 4/2015 | Shipley et al. | |
| 9,005,273 B2 | 4/2015 | Salahieh et al. | |
| 9,011,515 B2 | 4/2015 | Schweich et al. | |
| 9,011,523 B2 | 4/2015 | Seguin | |

(56) References Cited

U.S. PATENT DOCUMENTS

| | | |
|---|---|---|
| 9,011,530 B2 | 4/2015 | Reich et al. |
| 9,017,408 B2 | 4/2015 | Siegal et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,056,009 B2 | 6/2015 | Keränen |
| 9,061,120 B2 | 6/2015 | Osypka et al. |
| 9,078,747 B2 * | 7/2015 | Conklin ............... A61F 2/2418 |
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 | 3/2016 | Wilson et al. |
| 9,295,547 B2 | 3/2016 | Costello et al. |
| 9,301,756 B2 | 4/2016 | Wardle |
| 9,301,836 B2 | 4/2016 | Buchbinder et al. |
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 | 10/2016 | Zipory et al. |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,572,662 B2 | 2/2017 | Morriss et al. |
| 9,579,196 B2 | 2/2017 | Morriss et al. |
| 9,579,198 B2 | 2/2017 | Deem et al. |
| 9,585,751 B2 | 3/2017 | Morriss et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 | 2/2018 | Börtlein et al. |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Ratz et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,502 B2 | 6/2018 | Nasr et al. |
| 9,999,504 B2 | 6/2018 | Czyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,827 B2 | 7/2018 | Morriss et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 * | 7/2018 | Spence ............... A61F 2/2409 |
| 10,034,750 B2 | 7/2018 | Morriss et al. |
| 10,039,637 B2 | 8/2018 | Maimon et al. |
| 10,045,846 B2 | 8/2018 | Bonyuet et al. |
| 10,052,198 B2 * | 8/2018 | Chau ............... A61F 2/2418 |
| 10,052,199 B2 | 8/2018 | Spence et al. |
| 10,058,318 B2 | 8/2018 | Tegzes |
| 10,058,321 B2 | 8/2018 | Sampson et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi et al. |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,226,339 B2 * | 3/2019 | Spence ............... A61F 2/2418 |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahieh et al. |
| 10,433,961 B2 | 10/2019 | McLean |
| 10,463,479 B2 * | 11/2019 | Manash ............... A61F 2/2436 |
| 10,470,881 B2 | 11/2019 | Noe et al. |
| 10,478,291 B2 | 11/2019 | Nguyen et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |

(56) References Cited

U.S. PATENT DOCUMENTS

| | | | |
|---|---|---|---|
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |
| 10,603,165 B2 | 3/2020 | Maimon et al. |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,351 B2 * | 7/2020 | Griffin ............ A61F 2/2418 |
| 10,722,352 B2 | 7/2020 | Spence |
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,912,644 B2 * | 2/2021 | Argento ............ A61F 2/2418 |
| 10,973,629 B2 | 4/2021 | Levi et al. |
| 10,973,630 B2 | 4/2021 | Tonianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,103,345 B2 | 8/2021 | Levi et al. |
| 11,147,670 B2 | 10/2021 | Hayoz et al. |
| 11,234,818 B2 | 2/2022 | Zerkowski et al. |
| 11,547,563 B2 | 1/2023 | Keränen et al. |
| 11,672,657 B2 * | 6/2023 | Argento ............ A61F 2/2466 623/2.11 |
| 11,833,034 B2 * | 12/2023 | Argento ............ A61F 2/2418 |
| 11,986,389 B2 * | 5/2024 | Argento ............ A61F 2/2433 |
| 12,053,371 B2 * | 8/2024 | Adamek-Bowers ......... A61F 2/2409 |
| 2002/0173841 A1 | 11/2002 | Ortiz et al. |
| 2003/0114913 A1 | 6/2003 | Spenser et al. |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137694 A1 | 6/2005 | Haug et al. |
| 2005/0137696 A1 | 6/2005 | Salahieh et al. |
| 2005/0165344 A1 | 7/2005 | Dobak, III |
| 2005/0240202 A1 | 10/2005 | Shennib et al. |
| 2005/0277839 A1 | 12/2005 | Alderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0195134 A1 | 8/2006 | Crittenden |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0027533 A1 | 2/2007 | Douk |
| 2007/0038292 A1 | 2/2007 | Danielpour |
| 2007/0051377 A1 | 3/2007 | Douk et al. |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0030504 A1 * | 1/2009 | Weber ............ A61L 31/16 623/1.42 |
| 2009/0088836 A1 | 4/2009 | Bishop et al. |
| 2009/0093826 A1 | 4/2009 | Warder-Gabaldon |
| 2009/0138079 A1 | 5/2009 | Tuval et al. |
| 2009/0157174 A1 | 6/2009 | Yoganathan et al. |
| 2009/0192601 A1 | 7/2009 | Raffee et al. |
| 2009/0209950 A1 | 8/2009 | Starksen |
| 2009/0222026 A1 | 9/2009 | Rothstein et al. |
| 2009/0276040 A1 | 11/2009 | Rowe et al. |
| 2009/0299471 A1 * | 12/2009 | Keranen ............ A61F 2/2442 623/2.37 |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0076549 A1 * | 3/2010 | Keidar ............ A61F 2/2466 623/2.36 |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0040366 A1 * | 2/2011 | Goetz ............ A61F 2/91 623/1.15 |
| 2011/0046600 A1 | 2/2011 | Crank |
| 2011/0224785 A1 | 9/2011 | Hacohen |
| 2011/0245911 A1 * | 10/2011 | Quill ............ A61F 2/2418 623/2.11 |
| 2011/0288637 A1 | 11/2011 | De |
| 2011/0313515 A1 | 12/2011 | Quadri et al. |
| 2011/0319989 A1 | 12/2011 | Lane et al. |
| 2012/0022633 A1 * | 1/2012 | Olson ............ A61F 2/2436 623/2.11 |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277734 A1 | 11/2012 | Geotz et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0116779 A1 | 5/2013 | Weber |
| 2013/0123912 A1 | 5/2013 | Tung et al. |
| 2013/0172992 A1 * | 7/2013 | Gross ............ A61B 17/068 623/2.11 |
| 2013/0253643 A1 | 9/2013 | Rolando et al. |
| 2013/0274873 A1 | 10/2013 | Delaloye et al. |
| 2013/0325110 A1 | 12/2013 | Khalil et al. |
| 2014/0005768 A1 | 1/2014 | Thomas et al. |
| 2014/0031928 A1 | 1/2014 | Murphy et al. |
| 2014/0081154 A1 | 5/2014 | Toth |
| 2014/0200649 A1 | 7/2014 | Essinger et al. |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0277382 A1 | 9/2014 | Dolan et al. |
| 2014/0277409 A1 | 9/2014 | Börtlein et al. |
| 2014/0324163 A1 | 10/2014 | Keränen et al. |
| 2014/0379074 A1 | 12/2014 | Spence et al. |
| 2015/0005764 A1 | 1/2015 | Hanson et al. |
| 2015/0018876 A1 | 1/2015 | Ewers et al. |
| 2015/0039082 A1 * | 2/2015 | Keranen ............ A61F 2/2418 623/2.11 |
| 2015/0051709 A1 | 2/2015 | Vasquez et al. |
| 2015/0134055 A1 | 5/2015 | Spence et al. |
| 2015/0173897 A1 | 6/2015 | Raanani et al. |
| 2015/0250480 A1 | 9/2015 | Featherstone |
| 2015/0265403 A1 | 9/2015 | Keränen |

(56) References Cited

U.S. PATENT DOCUMENTS

| | | |
|---|---|---|
| 2015/0272737 A1 | 10/2015 | Dale et al. |
| 2015/0297346 A1 | 10/2015 | Duffy et al. |
| 2015/0305863 A1 | 10/2015 | Gray et al. |
| 2015/0327994 A1 | 11/2015 | Morriss et al. |
| 2015/0328000 A1 | 11/2015 | Ratz et al. |
| 2015/0335290 A1 | 11/2015 | Hunter |
| 2015/0335426 A1 | 11/2015 | Lim et al. |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0089126 A1 | 3/2016 | Guo |
| 2016/0095705 A1 | 4/2016 | Keränen et al. |
| 2016/0113764 A1 | 4/2016 | Sheahan et al. |
| 2016/0143689 A1 | 5/2016 | Ditter |
| 2016/0143731 A1 | 5/2016 | Backus et al. |
| 2016/0166380 A1 | 6/2016 | Seguin et al. |
| 2016/0199177 A1* | 7/2016 | Spence ............... A61F 2/243 623/2.38 |
| 2016/0206853 A1 | 7/2016 | Bolduc et al. |
| 2016/0228247 A1 | 8/2016 | Maimon et al. |
| 2016/0235526 A1 | 8/2016 | Lashinski et al. |
| 2016/0235529 A1 | 8/2016 | Ma et al. |
| 2016/0242902 A1 | 8/2016 | Morriss et al. |
| 2016/0242906 A1 | 8/2016 | Morriss et al. |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2016/0346080 A1 | 12/2016 | Righini et al. |
| 2017/0056163 A1 | 3/2017 | Tayeb et al. |
| 2017/0071732 A1 | 3/2017 | Conklin et al. |
| 2017/0079790 A1 | 3/2017 | Vidlund et al. |
| 2017/0112624 A1 | 4/2017 | Patel |
| 2017/0119524 A1 | 5/2017 | Salahieh et al. |
| 2017/0128203 A1 | 5/2017 | Zhang et al. |
| 2017/0128204 A1 | 5/2017 | Morriss et al. |
| 2017/0143481 A1 | 5/2017 | Morriss et al. |
| 2017/0156723 A1 | 6/2017 | Keating et al. |
| 2017/0165057 A9 | 6/2017 | Morriss et al. |
| 2017/0189177 A1 | 7/2017 | Schweich et al. |
| 2017/0216025 A1 | 8/2017 | Nitzan et al. |
| 2017/0224479 A1* | 8/2017 | Seguin ............... A61F 2/2436 |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0311937 A1 | 11/2017 | Bambury et al. |
| 2017/0348099 A1 | 12/2017 | Mendelson et al. |
| 2018/0021546 A1 | 1/2018 | McDermott et al. |
| 2018/0049873 A1 | 2/2018 | Manash et al. |
| 2018/0055628 A1 | 3/2018 | Patel et al. |
| 2018/0092763 A1 | 4/2018 | Dagan et al. |
| 2018/0110622 A1 | 4/2018 | Gregg et al. |
| 2018/0116790 A1 | 5/2018 | Ratz et al. |
| 2018/0133003 A1 | 5/2018 | Levi |
| 2018/0153690 A1* | 6/2018 | Spence ............... A61F 2/2418 |
| 2018/0177592 A1 | 6/2018 | Benichou et al. |
| 2018/0177594 A1* | 6/2018 | Patel ............... A61F 2/2436 |
| 2018/0206982 A1 | 7/2018 | Haivatov et al. |
| 2018/0206986 A1 | 7/2018 | Noe et al. |
| 2018/0206992 A1 | 7/2018 | Brown |
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Sheps et al. |
| 2018/0228610 A1 | 8/2018 | Lashinski et al. |
| 2018/0235443 A1 | 8/2018 | Smith et al. |
| 2018/0250126 A1 | 9/2018 | O'Connor et al. |
| 2018/0250132 A1 | 9/2018 | Ketai et al. |
| 2018/0263764 A1 | 9/2018 | Manash et al. |
| 2018/0280171 A1 | 10/2018 | Gloss et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'Ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1 | 11/2018 | Patel et al. |
| 2018/0325665 A1 | 11/2018 | Gurovich et al. |
| 2018/0333259 A1 | 11/2018 | Dibie |
| 2018/0344303 A1 | 12/2018 | Bambury et al. |
| 2018/0344454 A1 | 12/2018 | Mauch et al. |
| 2018/0344459 A1 | 12/2018 | Spence et al. |
| 2018/0344971 A1 | 12/2018 | Suzuki et al. |
| 2018/0360600 A1 | 12/2018 | Zhuang et al. |
| 2018/0368830 A1 | 12/2018 | O'Carroll et al. |
| 2019/0000614 A1 | 1/2019 | Morriss et al. |
| 2019/0000615 A1 | 1/2019 | Tayeb et al. |
| 2019/0000625 A1 | 1/2019 | O'Carroll et al. |
| 2019/0008635 A1 | 1/2019 | Francis et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0060069 A1 | 2/2019 | Maimon et al. |
| 2019/0060071 A1 | 2/2019 | Lane et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0142589 A1 | 5/2019 | Basude |
| 2019/0159770 A1 | 5/2019 | Rohl et al. |
| 2019/0160292 A1 | 5/2019 | Peichel et al. |
| 2019/0167425 A1 | 6/2019 | Reich et al. |
| 2019/0183649 A1 | 6/2019 | Allen et al. |
| 2019/0192288 A1 | 6/2019 | Levi et al. |
| 2019/0192294 A1 | 6/2019 | Spence et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0209320 A1 | 7/2019 | Drasler et al. |
| 2019/0231520 A1 | 8/2019 | Desrosiers et al. |
| 2019/0240023 A1 | 8/2019 | Spence et al. |
| 2019/0246916 A1 | 8/2019 | Kuraguntla et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0078000 A1 | 3/2020 | Rajagopal et al. |
| 2020/0093601 A1 | 3/2020 | Neustadter |
| 2020/0107932 A1 | 4/2020 | Rabito et al. |
| 2020/0107933 A1 | 4/2020 | Oba |

(56) References Cited

U.S. PATENT DOCUMENTS

| | | |
|---|---|---|
| 2020/0113586 A1 | 4/2020 | Karasic et al. |
| 2020/0113685 A1 | 4/2020 | Miller et al. |
| 2020/0113696 A1 | 4/2020 | Ekvall et al. |
| 2020/0138575 A1 | 5/2020 | Tuval |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0275921 A1 | 9/2020 | Gilmore et al. |
| 2020/0276017 A1 | 9/2020 | Subramanian et al. |
| 2020/0297489 A1 | 9/2020 | Bishop et al. |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0161688 A1 | 6/2021 | Shahriari |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0228343 A1 | 7/2021 | Scheinblum et al. |
| 2022/0054261 A1 | 2/2022 | Argento et al. |
| 2023/0105492 A1 | 4/2023 | Argento et al. |
| 2023/0118748 A1 | 4/2023 | Argento |
| 2023/0165679 A1 | 6/2023 | Boyd et al. |
| 2023/0225861 A1 | 7/2023 | Argento et al. |
| 2024/0293217 A1 | 9/2024 | Cartledge et al. |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 107690323 A | 2/2018 |
| CN | 111110401 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| DE | 102014102650 A1 | 9/2015 |
| EP | 1105181 B1 | 2/2004 |
| EP | 1432369 B1 | 2/2008 |
| EP | 2374415 A1 | 10/2011 |
| EP | 2907479 A1 | 8/2015 |
| EP | 3037064 A1 | 6/2016 |
| EP | 3158975 A1 | 4/2017 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2011506017 A | 3/2011 |
| JP | 2012531270 A | 12/2012 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/007873 A1 | 1/2007 |
| WO | WO2007/081820 A1 | 7/2007 |
| WO | WO2010/141847 A1 | 12/2010 |
| WO | WO2011/025945 A1 | 3/2011 |
| WO | WO2012/087842 A1 | 6/2012 |
| WO | WO2012/145545 A1 | 10/2012 |
| WO | WO2013/190910 A1 | 12/2013 |
| WO | WO2015/127264 A1 | 8/2015 |
| WO | WO2015/173609 A1 | 11/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO-2017151566 A1 | 9/2017 |
| WO | WO2017/214098 A1 | 12/2017 |
| WO | WO2018/025260 A1 | 2/2018 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO-2019010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/102484 A1 | 5/2019 |
| WO | WO-2019086958 A1 | 5/2019 |
| WO | WO2019/116369 A1 | 6/2019 |
| WO | WO-2019118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/082039 A1 | 4/2020 |
| WO | WO2020/123719 A1 | 6/2020 |
| WO | WO2020/157018 A1 | 8/2020 |
| WO | WO2020/163112 A1 | 8/2020 |
| WO | WO2020/210685 A8 | 10/2020 |
| WO | WO2020/236830 A1 | 11/2020 |
| WO | WO2020/247907 A1 | 12/2020 |

(56) References Cited

FOREIGN PATENT DOCUMENTS

WO    WO2021/028867 A1    2/2021
WO    WO2021/034497 A1    2/2021

OTHER PUBLICATIONS

Argento et al.; U.S. Appl. No. 16/594,946 entitled "Prosthetic cardiac valve devices, systems, and methods," filed Oct. 7, 2019.
Argento et al.; U.S. Appl. No. 16/723,537 entitled "Prothetic cardiac valve devices, systems, and methods," filed Dec. 20, 2019.
Argento et al.; U.S. Appl. No. 16/824,576 entitled "Prosthetic cardiac valve devices, systems, and methods," filed Mar. 19, 2020.
PCT/US2019/47842 International Search Report dated Jan. 2, 2020.
Argento et al.; U.S. Appl. No. 17/170,717 entitled "Prosthetic cardiac valve devices, systems, and methods," filed Feb. 8, 2021.
Argento et al.; U.S. Appl. No. 17/286,724 entitled "Adjustable medical device," filed Apr. 19, 2021.
Salahieh et al.; U.S. Appl. No. 17/543,555 entitled "Flared prosthetic cardiac valve delivery devices and systems," filed Dec. 6, 2021.
Yang et al.; U.S. Appl. No. 17/651,040 entitled "Anchor for prosthetic cardiac valve delivery devices and systems".
Salahieh.; U.S. Appl. No. 17/655,978 entitled "Anchor position verification for prosthetic cardiac valve devices," filed Mar. 22, 2022.
Saul; U.S. Appl. No. 17/773,193 entitled "Prosthetic cardiac valve delivery devices, systems, and methods," filed Apr. 29, 2022.
Argento et al.; U.S. Appl. No. 17/931,408 entitled "Prosthetic cardiac valve devices, systems, and methods," filed Sep. 12, 2022.
Adamek-Bowers et al.; U.S. Appl. No. 18/043,458 entitled "Prosthetic valve delivery system," filed Feb. 28, 2023.
Backus et al.; U.S. Appl. No. 18/004,609 entitled "Valve delivery system," filed Jan. 6, 2023.
Mulcahy et al.; U.S. Appl. No. 18/043,480 entitled "Prosthetic cardiac valve delivery devices, systems, and methods," filed Feb. 28, 2023.
Adamek-Bowers et al.; U.S. Appl. No. 18/043,499 entitled "Interface for prosthetic cardiac valve and delivery systems," filed Feb. 28, 2023.
Salahieh et al.; U.S. Appl. No. 18/043,519 entitled "Flared prosthetic cardiac valve delivery devices and systems," filed Feb. 28, 2023.
Scott et al.; U.S. Appl. No. 18/043,526 entitled "Access sheath for prosthetic cardiac valve delivery systems," filed Feb. 28, 2023.
Yang et al.; U.S. Appl. No. 18/043,542 entitled "Anchor for prosthetic cardiac valve devices," filed Feb. 28, 2023.
Argento et al.; U.S. Appl. No. 18/246,307 entitled "Systems, methods, and devices for expandable sensors," filed Mar. 22, 2023.
Argento et al.; U.S. Appl. No. 18/246,311 entitled "Prosthetic cardiac valve sensor devices, systems, and methods with imaging," filed Mar. 22, 2023.
Argento et al.; U.S. Appl. No. 18/185,330 entitled "Prosthetic cardiac valve devices, systems, and methods," filed Mar. 16, 2023.
Adamek-Bowers et al.; U.S. Appl. No. 18/255,763 entitled "Mitral valve implants," filed Jun. 2, 2023.
Schaefer; Large heart valves—small heart valves; ISMAAP; Oct. 19, 2015; 5 pages; retrieved from the internet (https://www.ismaap.org/condition-detail/large-heart-valves-small-heart-valves/) on Mar. 21, 2023.
Argento et al.; U.S. Appl. No. 18/494,520 entitled "Prosthetic cardiac valve devices, systems, and methods," filed Oct. 25, 2023.
Mulcahy et al.; U.S. Appl. No. 18/573,816 entitled "Prosthetic cardiac valve delivery devices, systems, and methods," filed Dec. 22, 2023.
Boyd et al.; U.S. Appl. No. 18/688,735 entitled "Guide catheter for prosthetic cardiac valve delivery systems, " filed Mar. 1, 2024.
Adamek-Bowers et al.; U.S. Appl. No. 18/693,856 entitled "Tether delivery of cardiac valve," filed Mar. 20, 2024.
Yang et al.; U.S. Appl. No. 18/700,621 entitled "Cardiac valve prosthesis delivery system and methods of use," filed Apr. 11, 2024.
Argento et al.; U.S. Appl. No. 18/639,743 entitled "Prosthetic cardiac valve devices, systems and methods," filed Apr. 18, 2024.
Masterclass; Knit vs. Woven: Learn How to Identify the Two Fabric Types; Jun. 7, 2021; 13 pages; retrieved from the internet (https://www.masterclass.com/articles/knit-vs-woven-learn-how-to-identify-the-two-fabric-types) on Nov. 15, 2024.

* cited by examiner

PROSTHETIC CARDIAC VALVE DEVICES, SYSTEMS, AND METHODS

CROSS-REFERENCE

This application claims the benefit of U.S. Provisional Patent Application No. 62/720,853, filed on Aug. 21, 2018, entitled Prosthetic Cardiac Valve Devices, Systems, and Methods; which is incorporated herein for all purposes in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to treatment of heart disease, and more particularly, implantable valve prostheses and treatments for heart valve diseases.

BACKGROUND

Referring to FIGS. 1 and 2, the heart 2 includes four chambers connected by four valves. The upper part of the heart 2 includes the left atrium 25 and right atrium 5. The lower part includes the left ventricle 26 and right ventricle 6. The heart 2 and cardiovascular system operates like a closed circuit. The right side of the heart 2 receives de-oxygenated blood from the body and delivers the blood through the pulmonary artery 7 to the lungs where it becomes re-oxygenated. The oxygenated blood is returned to the left side of the heart 2, referred to as the systemic side, which delivers the oxygenated blood throughout the body.

Blood flow between the heart chambers is regulated by the valves. On the left side of the heart, the mitral valve 4 is located between the left atrium 25 and the left ventricle 26 and the aortic valve 9 is located between the left ventricle 26 and the aorta 1. On the right side of the heart 2, the pulmonary valve 3 is located between the right ventricle 6 and the pulmonary artery 7 and the tricuspid valve 8 is located between the right ventricle 6 and the right atrium 5.

All four of heart valves are passive one-way valves with "leaflets" which open and close in response to differential pressures. For example, in a healthy heart during systole the left ventricle 26 contracts and pushes blood out the aortic valve 9. In turn, the pressure in the left ventricle 26 causes the mitral valve 4 to close thereby preventing blood from going back into the left atrium 25 during systole.

A significant population will acquire valve disease in their lifetime. Congenital heart disease is also a significant problem. Patients with valvular disease have abnormal anatomy and/or function of at least one valve. Congenital valve abnormalities may be tolerated and/or treated palliatively for some years before developing into a life-threatening problem in later years. However, congenital heart disease may present life-threatening risk without notice. Patients may acquire valvular disease from rheumatic fever, heart failure, degenerative leaflet tissue, bacterial infection, and more.

Valvular disease may be caused by several factors as shown in FIGS. 3 to 5. FIG. 3 shows a healthy mitral valve 4. Referring to FIGS. 4 to 5 show a diseased mitral valve 4. The valve 4 in FIG. 4 suffers from insufficiency, also referred to as regurgitation. Such a valve 4 does not fully close and allows blood to flow retrograde. In this case, blood will flow back into the left atrium 25 during systole. FIG. 5 shows a mitral valve 4 with stenosis. Such a valve 4 does not open properly. Some valves 4 can have concomitant insufficiency and stenosis. Other diseases may also be present, such as Barlow's disease, which prevent the valve 4 from functioning properly. These diseases reduce cardiac output and force the heart 2 to work harder, thus increasing the risk of heart failure and chordae failures.

While medications may be used to treat the disease, in many cases the defective valve may need to be repaired or replaced at some point during the patient's lifetime. The native valve can be replaced with a mechanical valve or tissue valve. Mechanical valves have a disc or other member which opens and closes. Although mechanical valves are formed of biocompatible materials, they carry an increased risk of clotting. Thus, patients usually need to take anticoagulants for the remainder of their lives, which presents additional complications. Tissue valves can be formed of human or animal tissue, as well as polymeric materials. Tissue valves, unlike mechanical valves, do not typically require long-term use of anti-coagulants, but because they are formed of a living tissue they are not as widely available nor do they last as long as mechanical valves. Common tissue valves include porcine aortic valves mounted within a stent-like structure.

More recently there has been increased interest in less invasive procedures for implantation of prosthetic valves. One type of percutaneous procedure involves using a catheter to place a prosthetic valve inside of a diseased or injured heart valve.

Existing percutaneous procedures for valve repair still face many challenges. These challenges have limited the adoption of transcatheter procedures to certain patient populations and anatomies. Thus far, transcatheter devices are largely focused on aortic valve procedures and the sickest patient populations who may not be able to tolerate surgery. There is a continuing need for improved transcatheter devices which meet or exceed the performance and safety of surgical valves. Percutaneous valve replacement has also been limited to aortic valve procedures. While a large segment of the population suffers from tricuspid and mitral valve disease, the anatomy and function of these valves present challenges to transcatheter replacement. The aortic valve can be accessed via the femoral artery whereas the mitral valve, for example, typically requires a transseptal approach. The mitral valve anatomy presents more complexities to transcatheter procedures than the aortic valve. For example, as shown in FIG. 4, the mitral valve 4 includes two asymmetrical leaflets 4a, 4b and an irregularly-shaped annulus 4c. The mitral valve 4 also varies far more considerably patient-to-patient than the aortic valve. For these and other reasons, surgical replacement and percutaneous repair thus far are the only widely-available commercial treatments for mitral valve disease.

SUMMARY

It would therefore be desirable to provide a less invasive procedure for repair and replacement of heart valves, including the mitral valve, quicker surgical methods, a variety of different valve assemblies to accommodate the requirements of different patients, and/or prosthetic valves that can accommodate a variety of individual patients. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure relates to prosthetic cardiac devices, and in some embodiments, prosthetic heart valves such as catheter-based mitral valves.

In a first aspect, a heart valve prosthesis for replacing a diseased native valve in a patient is provided. The heart valve prosthesis includes a compressible and expandable frame structure and an anchor connected to an outer periphery of the frame structure. The anchor comprises a helical wire having a free end. The valve may further include a valve segment within the frame structure. The valve segment may include a biocompatible one-way valve.

In a second aspect, a heart valve prosthesis for replacing a diseased native valve in a heart of a patient is provided. The valve prosthesis comprises a compressible and expandable frame structure, a valve segment disposed within the frame structure, the valve segment comprising a biocompatible one-way valve, and an anchor connected to an outer periphery of the frame structure, wherein the anchor comprises a helical wire having a free end.

In some embodiments, the free end of the helical wire may be configured to guide the helical wire through a commissure of a native valve of a patient.

In some embodiments, the free end may comprise an atraumatic tip. For example, the free end may comprise a ball tip.

In some embodiments, the free end may be configured for piercing tissue.

In some embodiments, the anchor may comprise a first portion comprising the helical wire and another portion.

In some embodiments, the anchor may comprise a plurality of anchors. The plurality of anchors may comprise at least two helical wires having different diameters. Alternatively, or in combination, the plurality of anchors may comprise at least two helical wires having different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the frame structure may be configured for expanding within a native valve of a patient.

In some embodiments, the frame structure may have a compressed state sized and dimensioned for percutaneous insertion and an expanded state sized and dimensioned for implantation in a native valve of a patient.

In some embodiments, the frame structure may comprise first and second opposite ends, the first end extending above a native valve and the second end extending below the native valve when the valve prosthesis is positioned across the native valve.

In some embodiments, the frame structure may comprise an expandable stent.

In some embodiments, the frame structure may comprise a generally tubular expanded shape.

In some embodiments, the frame structure may comprise an expanded outer periphery and a compressed outer periphery when subject to an external radial force. The compressed outer periphery may be slightly smaller in diameter than the expanded outer periphery.

In some embodiments, the frame structure may be balloon-expandable.

In some embodiments, the frame structure may be self-expanding.

In some embodiments, at least a portion of the valve segment may be positioned within at least a portion of the frame structure.

In some embodiments, the valve segment may comprise at least one leaflet having an inner layer and an outer layer. The frame structure may be attached to the outer layer at one or more ends of the frame structure.

In some embodiments, the valve segment may comprise a plurality of leaflets. For example, the valve segment may comprise two leaflets.

In some embodiments, the helical wire may comprise a second end, and wherein the second end is attached to the frame structure. The helical wire may be attached to the frame structure only at the location of the second end.

In some embodiments, the anchor and the frame structure may be adapted to be independently and separately expanded.

In another aspect, a method of replacing a diseased native valve of a patient is provided. The method comprises loading a valve prosthesis into a delivery catheter, the valve prosthesis comprising an expandable frame structure carrying a biocompatible valve segment and an anchor attached to an outer periphery of the frame structure, the anchor comprising a wire having a free end; delivering the valve prosthesis to a target location above a native valve; inserting the valve prosthesis through the native valve to a position posterior the native valve; rotating the wire such that the free end wraps around at least a portion of chordae tendineae below the valve; and expanding the frame structure including the valve segment within the native valve.

In some embodiments, the method may further comprise anchoring the valve prosthesis by rotating the wire until the frame structure is positioned within leaflets of the native valve.

In some embodiments, the method may further comprise anchoring the valve prosthesis by rotating the wire until the wire tightens around the chordae tendineae.

In some embodiments, the frame structure may be balloon-expandable. Expanding the frame structure may comprise expanding a balloon within the frame structure.

In some embodiments, the frame structure may be self-expanding. Expanding the frame structure may comprise removing a sheath of the delivery device from the frame structure.

In some embodiments, the wire may be a helical wire.

In some embodiments, inserting the valve prosthesis may comprise guiding the free end of the wire through a commissure of the native valve. In some embodiments, rotating the wire may comprise rotating the wire through the commissure.

In another aspect, a heart valve prosthesis for replacing a diseased native valve in a patient is provided. The valve prosthesis comprises a compressible and expandable frame structure, a valve segment disposed within the frame structure comprising a biocompatible one-way valve, and an anchor connected to the frame structure and disposed radially outward from the frame structure, wherein the anchor comprises a helical member having a free end.

In some embodiments, the second end of the anchor may be connected to the frame structure.

In some embodiments, the helical member may comprise a wire or a flat ribbon.

These and other embodiments are described in further detail in the following description related to the appended drawing figures.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

Figure 1:
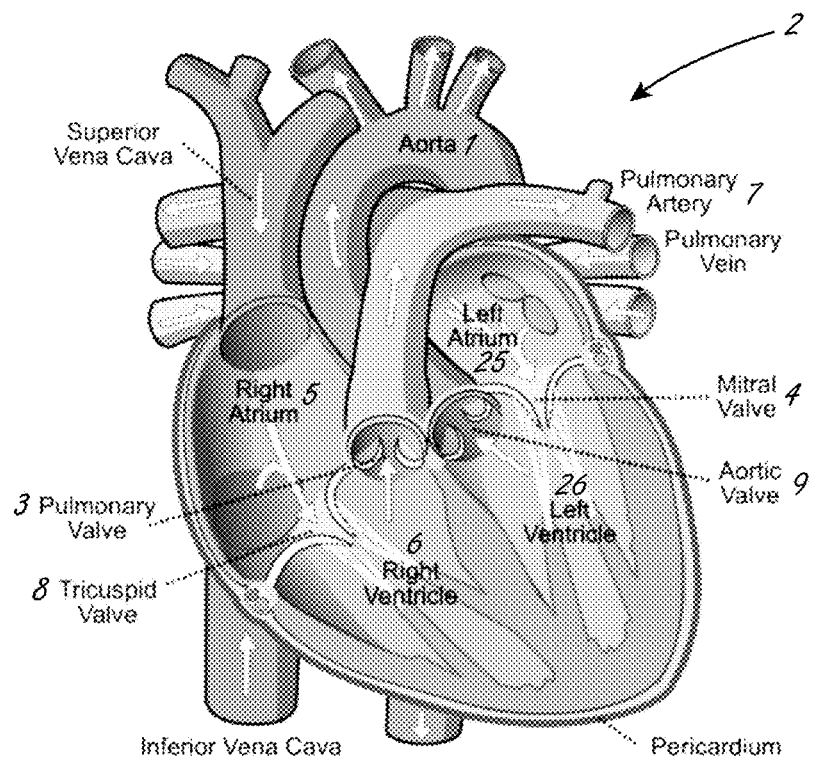
FIG. 1 is a schematic of a human heart illustrating the path of blood flow through the heart.

The devices and methods of the present disclosure have other features and advantages which will be apparent from or are set forth in more detail in the accompanying drawings, which are incorporated in and form a part of this specification, and the following Detailed Description, which together serve to explain the principles of the present invention.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for treatment of a diseased native valve of the heart, for example a mitral valve. However, one of skill in the art will appreciate that this is not intended to be limiting and the devices and methods disclosed herein may be used in other anatomical areas and in other surgical procedures.

For convenience in explanation and accurate definition in the appended claims, the terms "up" or "upper", "down" or "lower", "inside" and "outside" are used to describe features of the embodiments with reference to the positions of such features as displayed in the figures.

In many respects the modifications of the various figures resemble those of preceding modifications and the same reference numerals followed by subscripts "a", "b", "c", and "d" designate corresponding parts.

Figure 2:
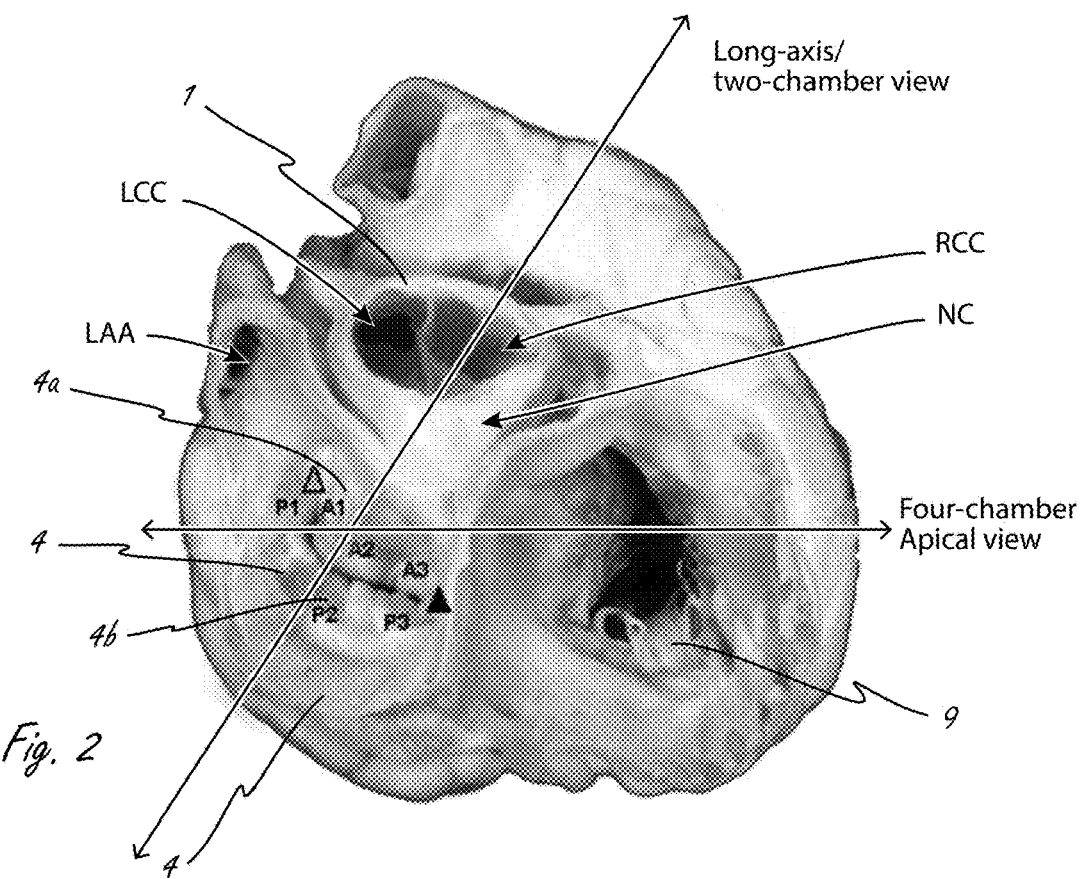
FIG. 2 is a cross-sectional view of a heart looking down through the mitral valve, aortic valve, and aorta.
Figure 3:
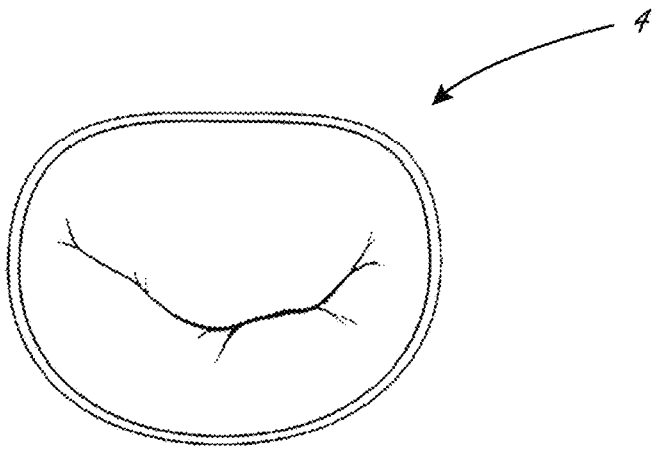
FIG. 3 is a schematic of a healthy mitral valve.

Turning now to the drawings, wherein like components are designated by like reference numerals throughout the various figures, attention is directed to FIGS. 1-5. FIG. 1 shows a human heart 2 and the blood flow pathways through the four chambers of the heart. FIG. 2 is a human heart 2 showing the mitral valve 4, aortic valve 9, and aorta 1. The mitral valve 4 includes two leaflets 4a, 4b. The anterior (aortic) leaflet 4a is adjacent the aorta 1. The posterior (mural) leaflet 4b is remote from the aorta 1. The aortic valve 9 includes three leaflets. In the current view, the heart 2 is in systole with the aortic valve 9 open and the mitral valve 4 closed. Whereas FIG. 1 illustrates a healthy heart 2, FIGS. 2-5 illustrate exemplary mitral valve 4 disease states which may be addressed by the prosthetic valve in accordance with the present disclosure. The prosthetic valve may also be used to treat functional regurgitation such as functional mitral regurgitation (FMR).

FIGS. 6-18 show an exemplary valve prosthesis 10 (also referred to herein as "valve device") for replacement of a diseased mitral valve in accordance with the present disclosure. The illustrated valve prosthesis 10 comprises a frame structure 12, a valve segment 14, and an anchor 15. FIGS. 6-10 show the valve prosthesis 10 in an expanded, deployed state. FIGS. 12-18 show the frame structure 12 without the valve segment 14. The frame structure 12 is in a collapsed state in FIGS. 12-15 and an expanded state in FIGS. 16-18. The anchor 15 is shown in a deployed state.

The exemplary valve prosthesis 10 will now be described with reference to FIGS. 6-11. In the illustrated embodiment, valve prosthesis 10 is configured for replacement of a native mitral valve. Valve 10 includes a frame structure 12, valve segment 14, and anchor 15. In the illustrated embodiment, the anchor includes a wire 20 formed in a helical or spiral shape around the frame structure.

Exemplary frame structure 12 is configured like a stent. The frame has an expanded state and a collapsed or compressed state. The compressed state is sized and dimensioned for percutaneous insertion and the expanded state sized and dimensioned for implantation in a native valve of a patient. In various embodiments, the frame structure 12 comprises an expanded outer periphery and a compressed outer periphery when subject to an external radial force, the compressed outer periphery being slightly smaller in diameter than the expanded outer periphery. The frame structure 12 is shown in the expanded, deployed state in FIG. 6. The frame structure 12 is shown in the collapsed, delivery state in FIG. 12.

The exemplary frame structure 12 is a scaffold in a diamond pattern formed from a shape memory material (e.g. NiTi). One of ordinary skill in the art will appreciate from the description herein that many other structures, materials, and configurations may be employed for the frame structure 12. For example, the frame structure 12 may be formed of a polymer of sufficient elasticity. The frame structure 12 may be formed of a combination of a metal and polymer, such as a metal (e.g. shape memory material) covered in polymer. The frame structure 12 may include a variety of patterns besides diamond shapes.

Valve prosthesis 10 includes a valve segment 14 within the frame structure 12. The exemplary valve segment 14 is expandable and collapsible. In the illustrated embodiment, the valve segment 14 is affixed within the frame structure 12 and expands and collapses with the frame structure 12. Valve segment is used somewhat interchangeably with prosthetic valve leaflet and generally refers to the prosthetic leaflets and frame. As used herein, "prosthetic valve" may refer to all manner of prosthetic and artificial replacement valves including tissue (biological) valves, tissue-engineered valves, polymer valves (e.g. biodegradable polymer valves), and even certain mechanical valves.

In the illustrated embodiment, frame structure 12 is a closed frame such that blood flow is forced through valve segment 14 therein. One or more skirts and/or seals may help force blood through valve segment 14.

Figure 11:
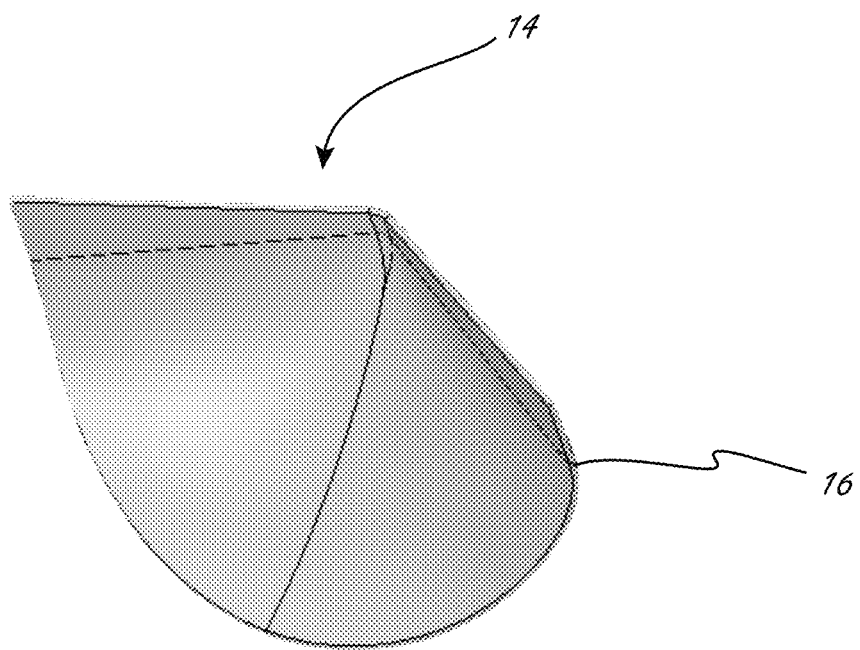
FIG. 11 is a perspective view of the prosthetic valve leaflet of the valve of FIG. 6, in accordance with embodiments.
Figure 12:
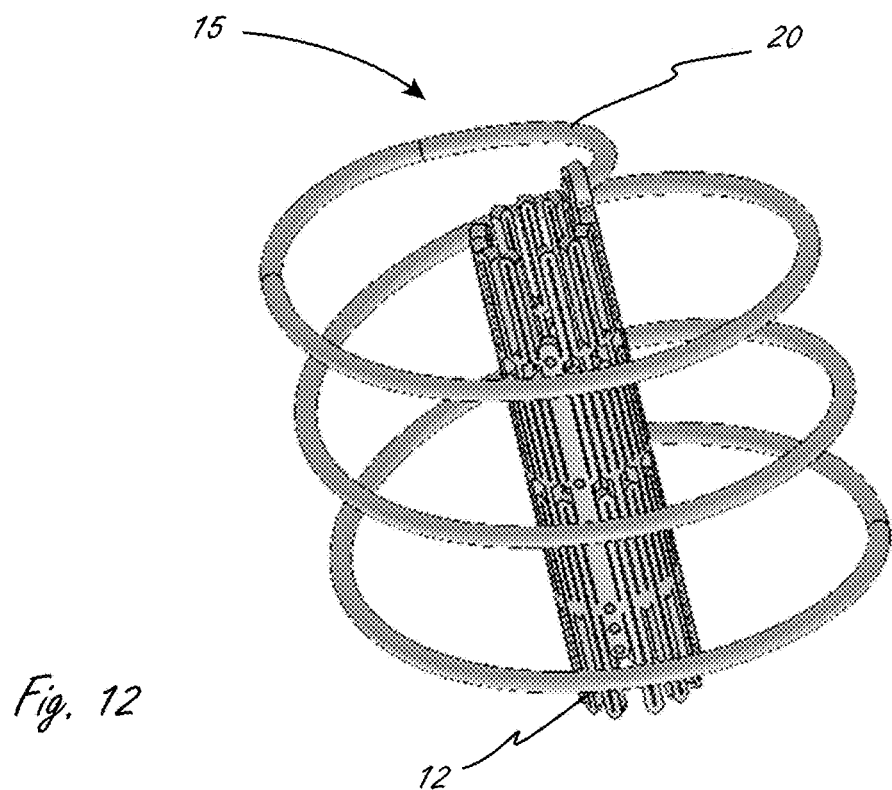
FIGS. 12 to 18 are several views of the frame structure of the valve of FIG. 6, in accordance with embodiments.
Figure 13:
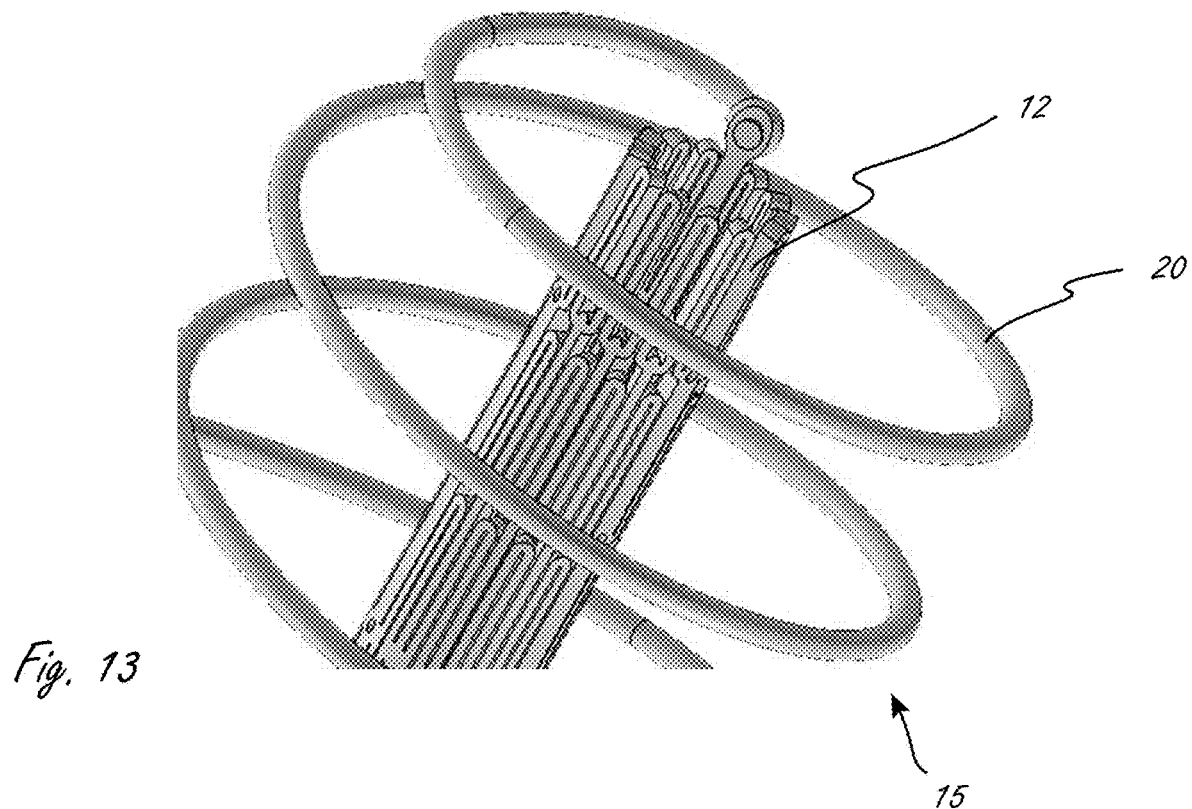
Figure 14:
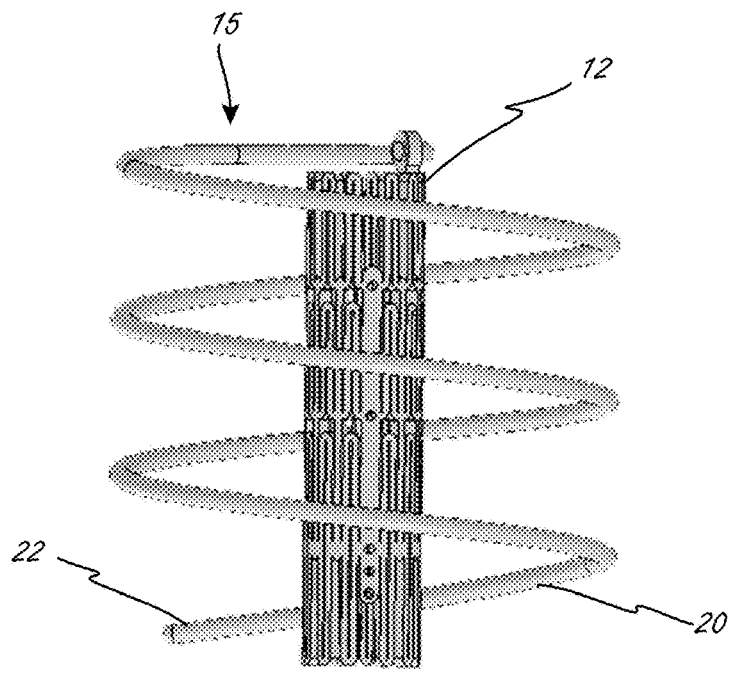
Figure 15:
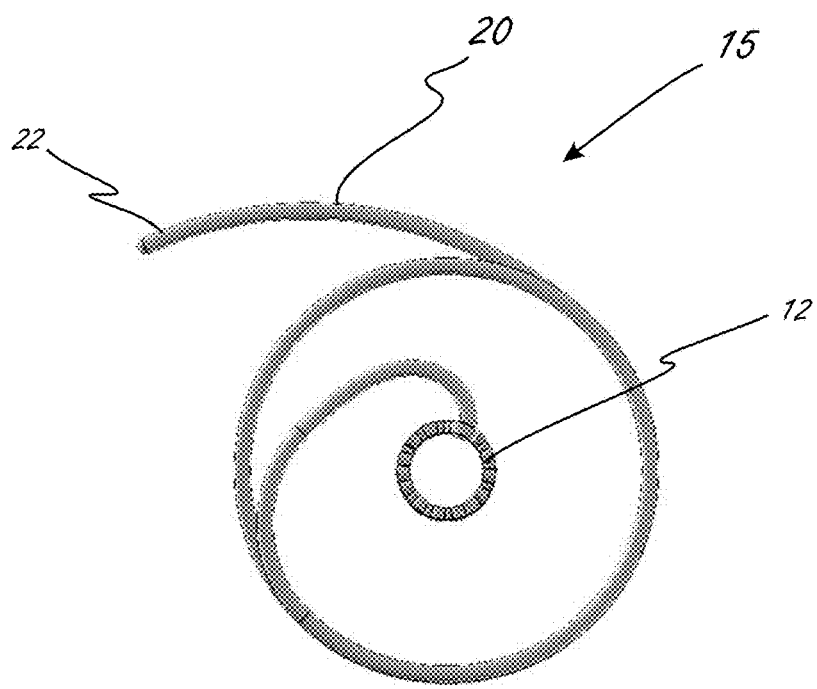
Figure 16:
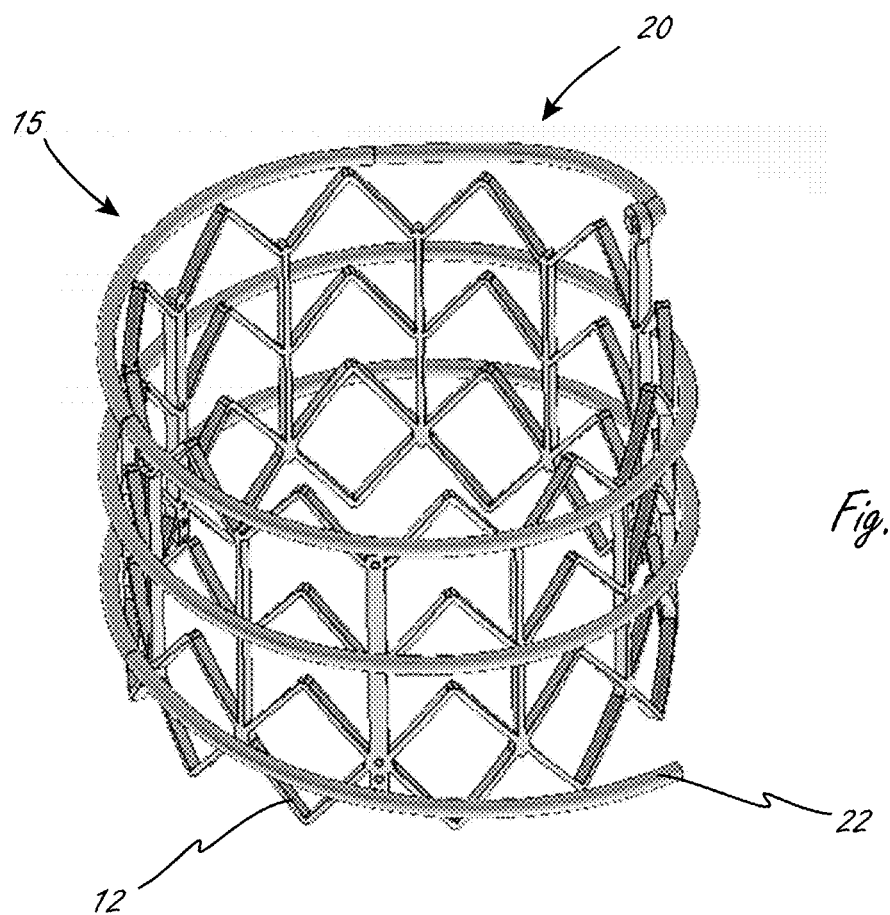
Figure 17:
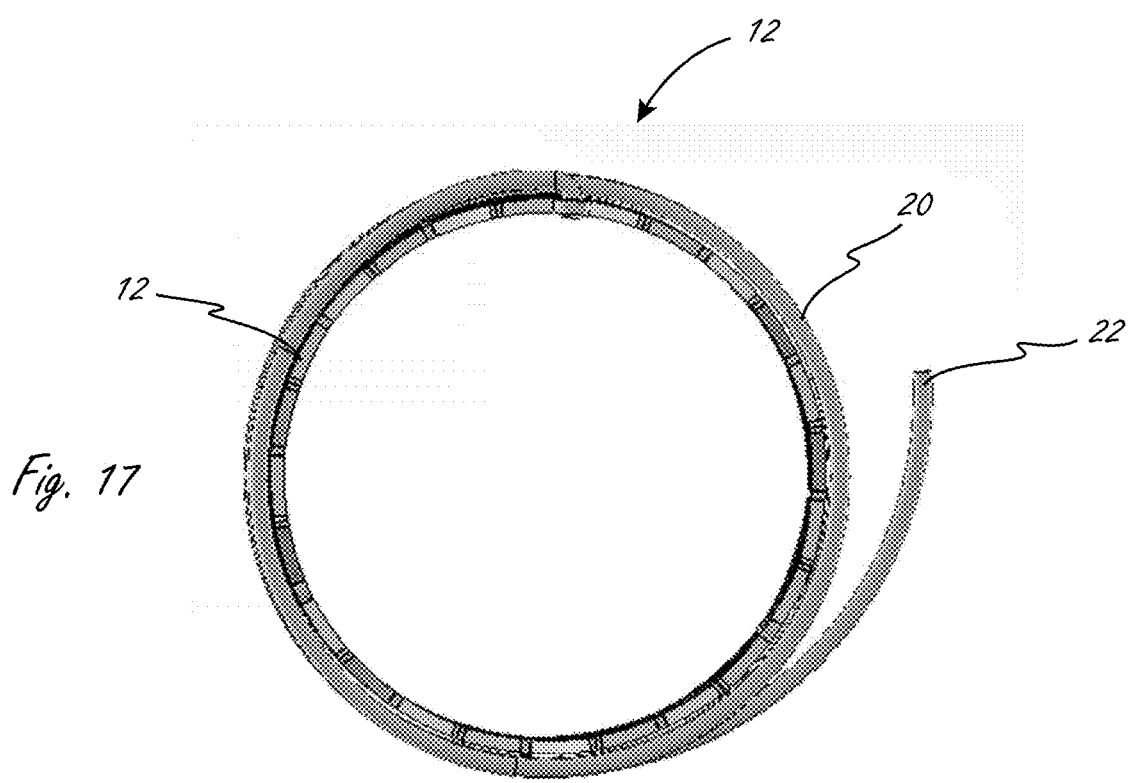
Figure 18:
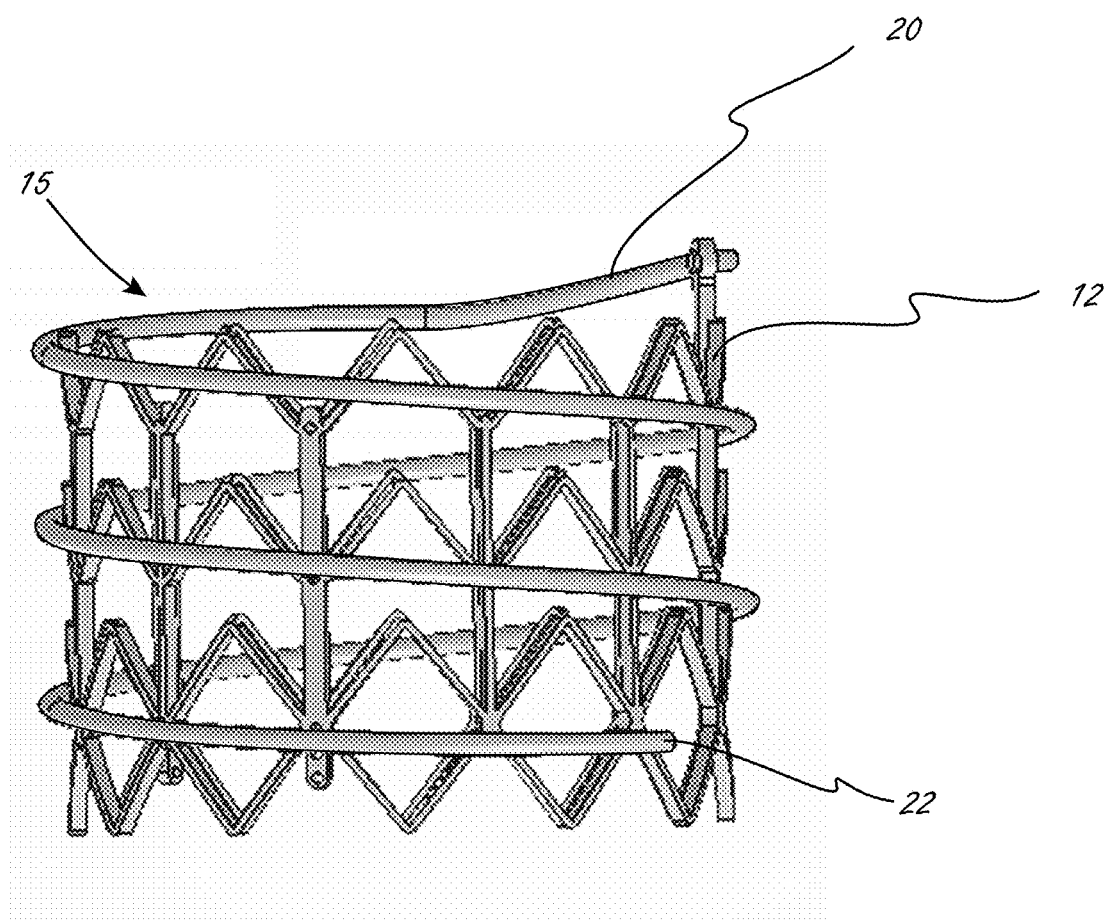

Valve segment 14 can be configured as would be understood by one of skill from the description herein. The valve segment 14 can be similar to existing transcatheter valves. The valve segment 14 can be similar to existing surgical tissue valves, and mechanical valves. In various embodiments, the valve segment 14 includes leaflets 16 formed of multi-layered materials for preferential function. At least one leaflet 16 may have an inner layer and an outer layer. In various embodiments, the leaflet 16 is connected to a valve structure which in turn is connected to the frame structure 12. The valve structure may be connected to the frame structure 12 before or after the frame structure 12 has been deployed adjacent a native valve. In various embodiments, the leaflet 16 is attached to the frame structure 12 directly. The leaflet 16 may have an inner layer and an outer layer, with the outer layer attached to the frame structure 12. The leaflet 16 may be attached to an end of the frame structure 12. Alternatively, or in combination, the leaflet 16 may be attached to an intermediate portion of the frame structure 12. In various embodiments, the valve segment 14 includes a plurality of leaflets 16, such as two, three, or more leaflets. In the illustrated embodiment, the valve segment 14 includes three leaflets 16 which are attached to frame structure 12. An exemplary leaflet 16 is shown in FIG. 11. The leaflet 16 is concave to permit flow in one direction. In particular, flow in one direction causes the leaflet(s) 16 to deflect open and flow in the opposite direction causes the leaflet(s) 16 to close.

Turning back to FIGS. 6-18, and more particularly FIGS. 12-18, an exemplary anchor 15 comprises a helical member, such as wire 20, having a free end 22. The other end of the wire 20 is attached to a top end of frame structure 12. In the illustrated embodiment, one end of the wire 20 is fixed to a strut of the frame structure 12. This end can be attached by suitable means as would be understood by one of skill in the art from the description herein including, but not limited to, a weld, an adhesive, and a mechanical fastener. In various embodiments, the helical wire 20 is attached to the frame structure only at the location of the second end.

Although referred to as an anchor, one will appreciate that anchor 15 does not require performing an anchor function in the traditional sense. As will be described in more detail below, the anchor guides valve prosthesis 10 into a desired position within a native valve. The anchor 15 may also mitigate against undesired entanglement and disturbances to the chordae tendineae and valve leaflets of the mitral valve.

Wire 20 is formed of a material having sufficient rigidity to hold a predetermined shape. In the exemplary embodiment, the wire 20 is formed of a shape memory material (e.g. NiTi). It may be desirable for at least an end portion to be relatively rigid such that it can exert a force to move chordae tendineae, while still retaining flexibility to be collapsed within a catheter. In various embodiments, the end portion (including free end 22) only needs sufficient rigidity to hold its shape and will deform under a load. For example, the end portion may be configured with similar rigidity to a guidewire, or slightly stiffer.

In various embodiments, the anchor 15 comprises a helical member. The helical member may comprise a helical wire or flat ribbon. The helical member may comprise a three-dimensional surface as described herein.

In various embodiments, the anchor 15 may comprise a first portion comprising the helical wire 20 and another portion. Alternatively or in combination, the anchor 15 may comprise a plurality of helical wires 20. For example, the anchor 15 may comprise at least two helical wires 20 having the same or different diameters. Alternatively or in combination, the anchor 15 may comprise at least two helical wires 20 having the same or different winding pitches.

In various embodiments, the anchor 15 may comprise a plurality of anchors, for example a plurality of helical wires 20 as described herein.

Figure 4:
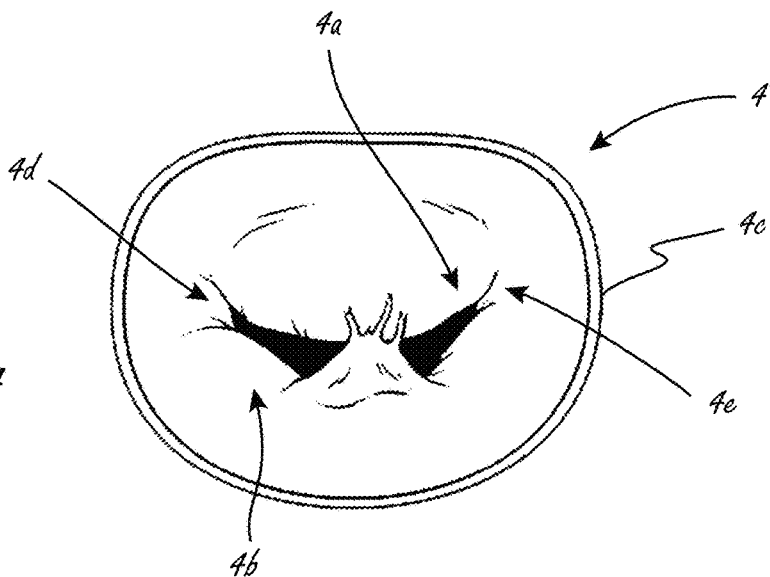
FIGS. 4 and 5 are schematics of diseased mitral valves.
Figure 5:
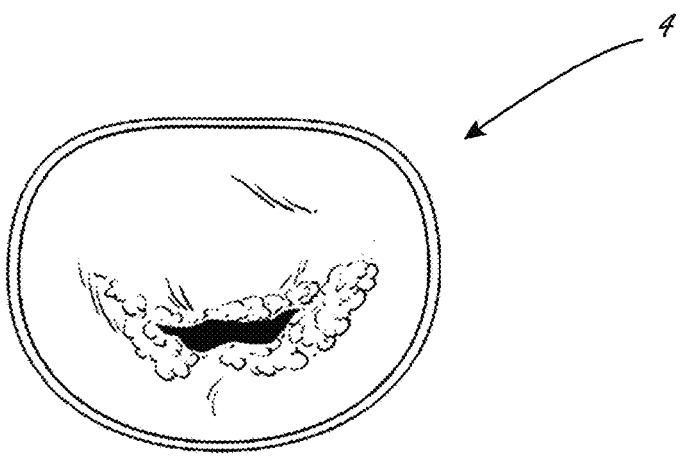
Figure 6:
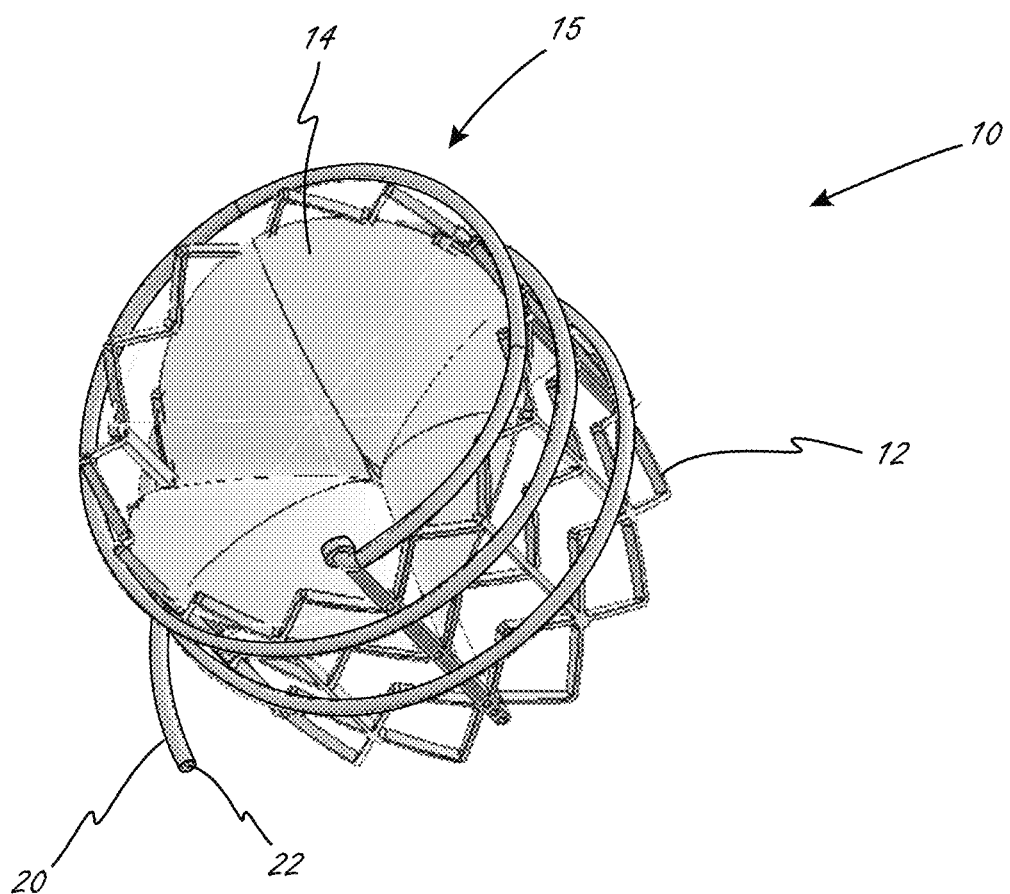
FIGS. 6 to 10 are several views of a percutaneous valve for replacement of a diseased native valve, in accordance with embodiments.
Figure 7:
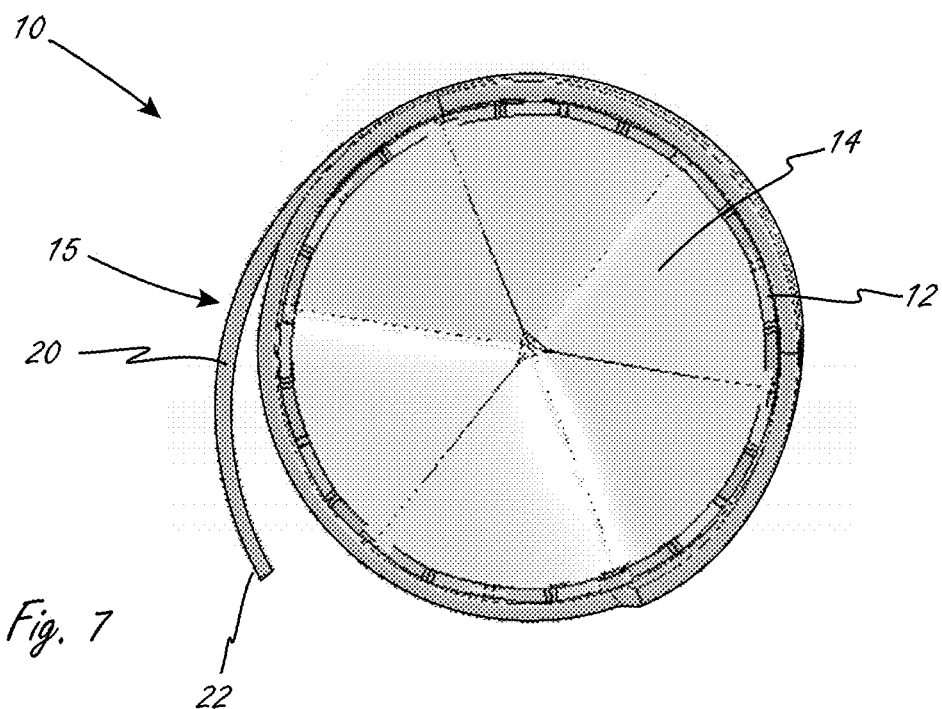
Figure 8:
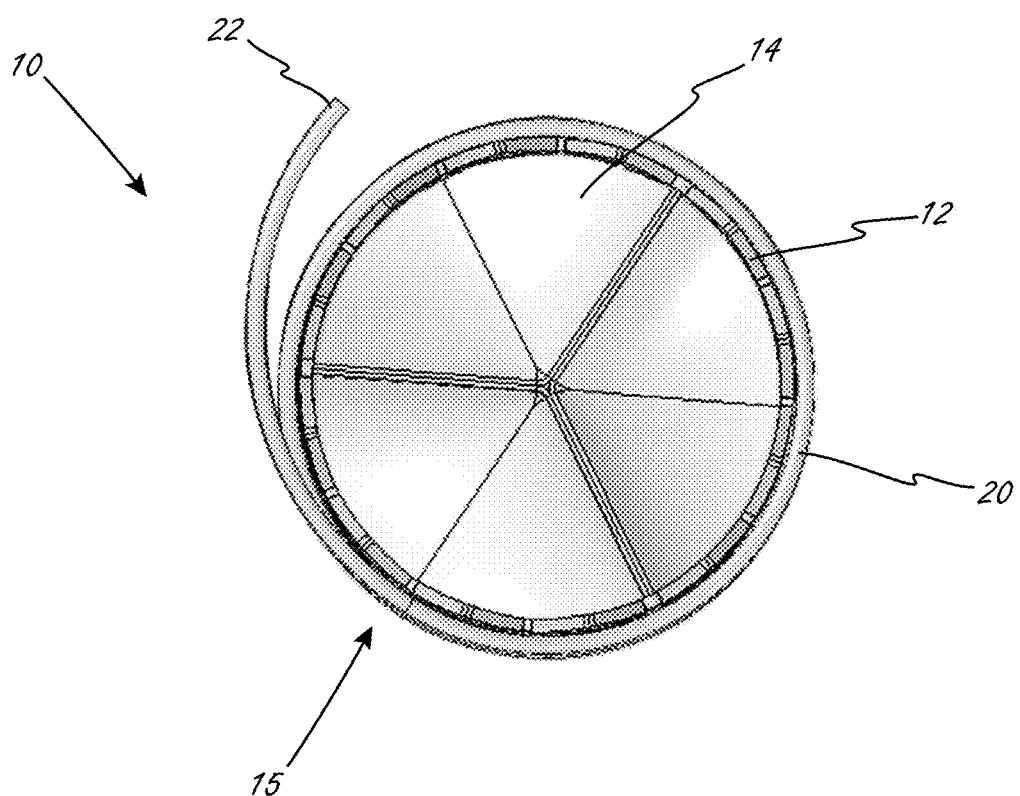
Figure 9:
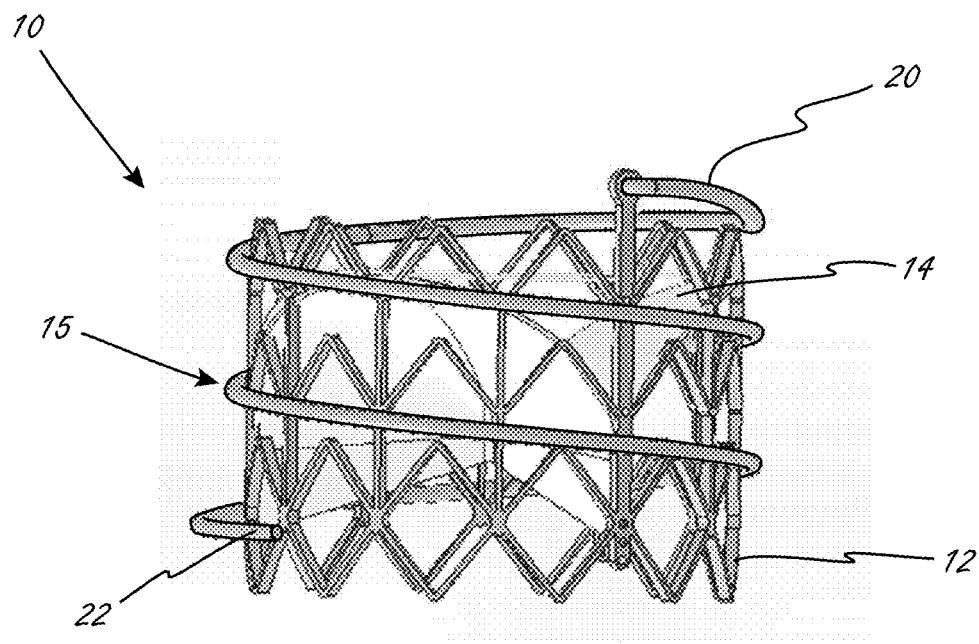
Figure 10:
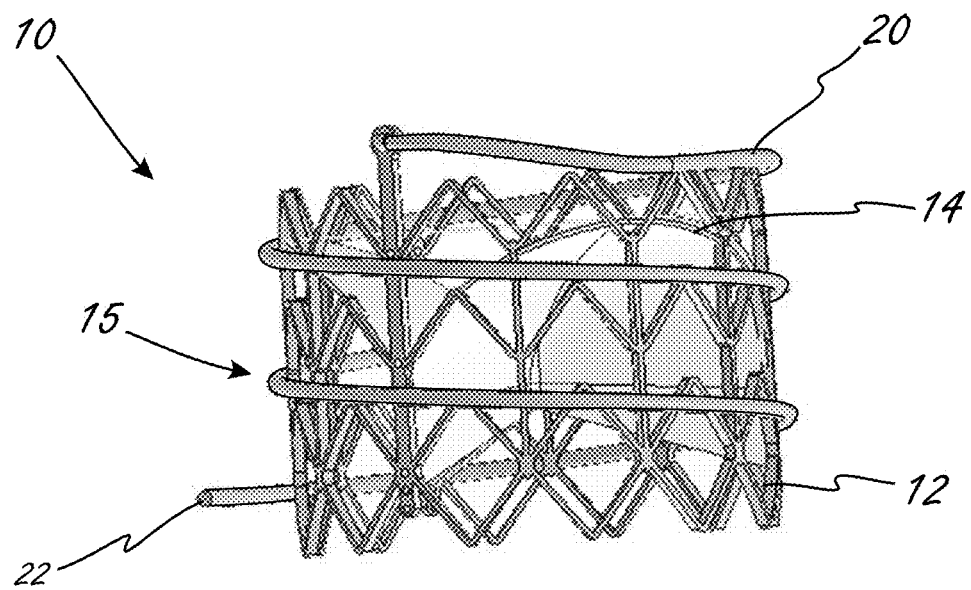

In the illustrated embodiment, valve prosthesis 10 is configured for replacing a mitral valve and free end 22 is configured for insertion through a commissure. FIG. 1 is a schematic of a human heart 2 having a mitral valve 4. FIGS. 2 and 4 show an exemplary mitral valve 4. As can be seen in the figures, several commissure points (anterolateral commissure 4d and posteromedial commissure 4e) are presented at the ends of the valve leaflets 4a, 4b.

With continued reference to FIGS. 6-18, the exemplary free end 22 is sized and dimensioned for insertion through one of the commissures. In the various embodiments, the free end 22 is configured to be atraumatic to avoid risk of injury to the valve tissue and leaflets. The free end 22 may be in the form of a blunt end, a ball tip, a curved tip (e.g., J-tip or pigtail), and other atraumatic shapes. In various embodiments, the free end 22 is configured with a sharp end to pierce tissue.

In various embodiments, wire 20 has varying stiffness along its length. The wire 20 may have two or more segments of differing stiffness and/or the stiffness may transition over its length. In various embodiments, wire 20 is attached to frame 12 at multiple points such that free end 22 is relatively flexible and the wire 20 is more rigid along portions where it is attached to the frame structure 12.

In various embodiments, free end 22 extends radially outward from frame structure 12, and in particular the remainder of wire 20. As will be described below, the free end 22 is configured to encircle a larger radius than the main coils of the wire 20. For example, when the main coils of wire 20 have a generally tubular shape, the free end 22 may extend radially outward from the tubular shape. When the main coils of wire 20 have a generally helical shape, the free end 22 may extend radially outward from the helical shape. When the main coils of wire 20 have a generally frustoconical shape, the free end 22 may extend radially outward from the frustoconical shape. The larger diameter facilitates capturing of the valve leaflets and/or chordae tendineae within the sweep of the free end 22 during rotation as will be described in more detail below.

The method of implanting valve prosthesis 10 in accordance with the present disclosure will now be described with reference to FIGS. 19-28. Although shown and described with respect to a mitral valve, one will understand that the principles described herein may be applied equally to other atrioventricular valves. Aspects of the procedure, delivery tool, and implanted valve prosthesis are similar to those described in U.S. Pat. Nos. 9,034,032; 9,005,273; 8,323, 336; 8,075,615; 7,621,948; and 7,175,656 and U.S. Pub. No. 2011/0288637, which are incorporated herein for all purposes in their entirety.

Figure 19:
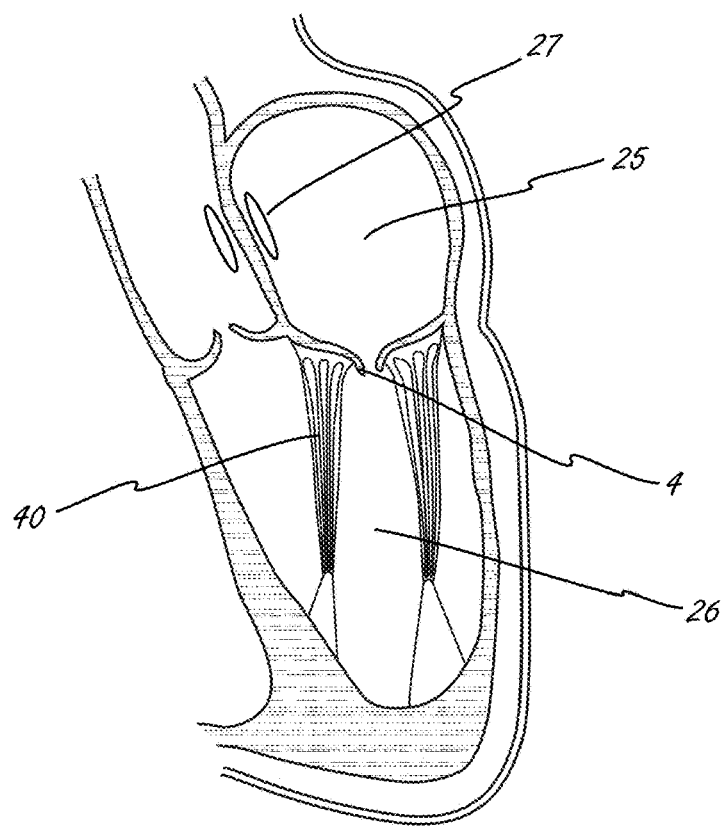
FIGS. 19 to 26 are several views of the method of implanting the valve of FIG. 6, in accordance with embodiments.

Prior to implantation, valve prosthesis 10 is collapsed and loaded into a delivery device 30, for example, a delivery catheter. The valve system is optionally primed before or after loading into the delivery catheter 30. FIG. 19 shows a cross-sectional side view of a heart 2 with a transseptal puncture 27 in the atrial septum thereof. The leaflets 42 of valve 4 do not fully prolapse and the patient is experiencing regurgitation.

Figure 20:
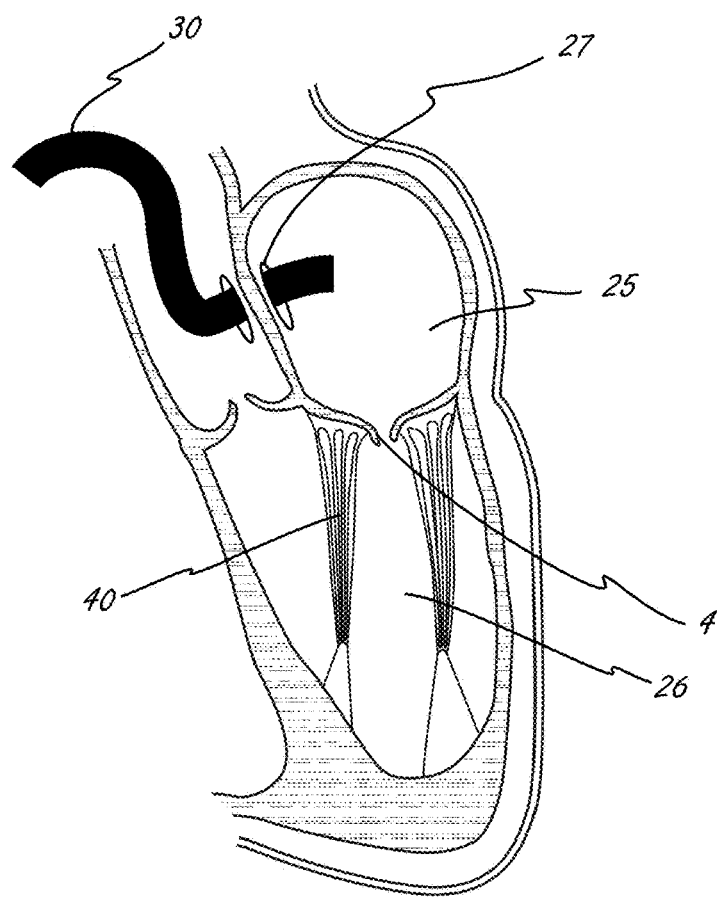

Next, the delivery catheter 30 is inserted through an introducer into a vessel. The delivery catheter 30 can be guided over a guidewire to a target location using the Seldinger technique. In the illustrated embodiment, the delivery catheter 30 is guided to the left atrium 25 through a transseptal puncture 27 in conventional fashion as shown in FIG. 20.

Figure 21:
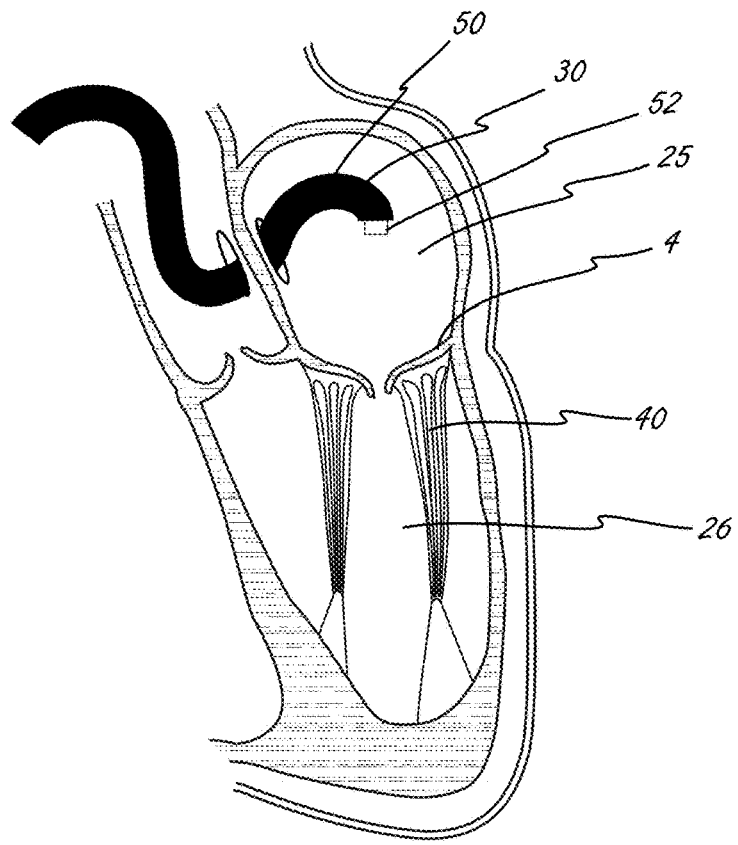
Figure 22:
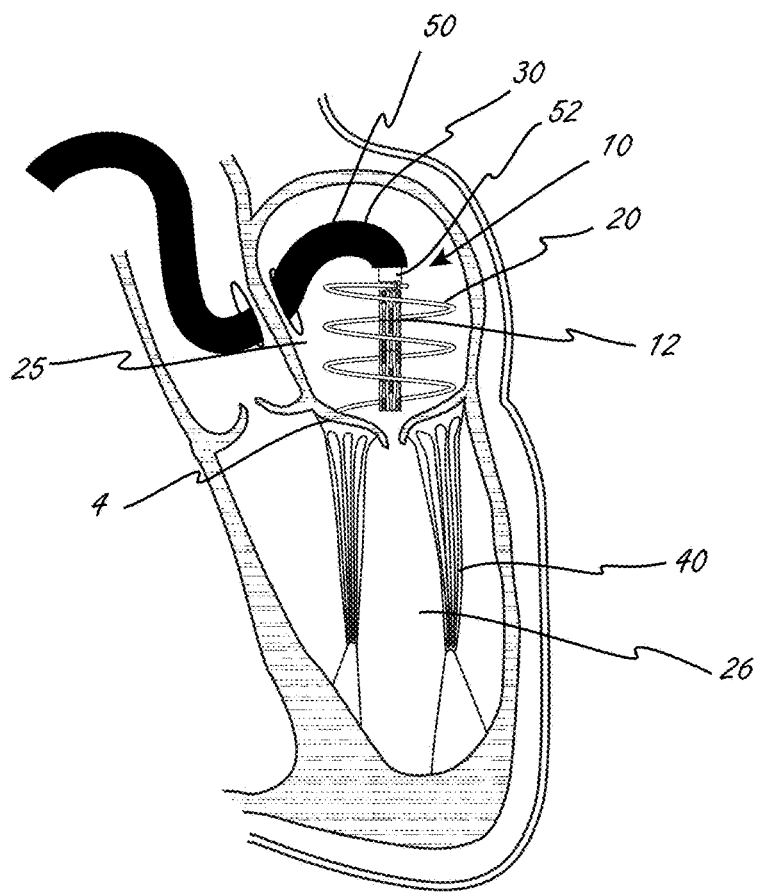

Turning to FIGS. 21-22, at this point, the end of the delivery catheter 30 is pointed towards the mitral valve 4. Valve prosthesis 10 is then pushed out of the distal end of delivery catheter 30. The delivery device 30 may comprise an outer catheter 50 and an inner catheter or shaft 52. In some embodiments, once the delivery device 30 is in position, the delivery tube 52 extends out of the outer catheter 50 to move valve device 10 distally towards the native valve 4. As the valve prosthesis 10 comes out from the delivery catheter 30, an anchor 15, such as wire 20, is deployed (e.g., from a straightened shape within the delivery device 30) to its pre-formed deployed shape and wraps around frame 12, which remains in its collapsed state as shown in FIG. 22. The valve prosthesis 10 is then aligned with the target native valve 4 so the axis of the prosthetic valve 10 is aligned with a central axis of the native valve 4.

Figure 23:
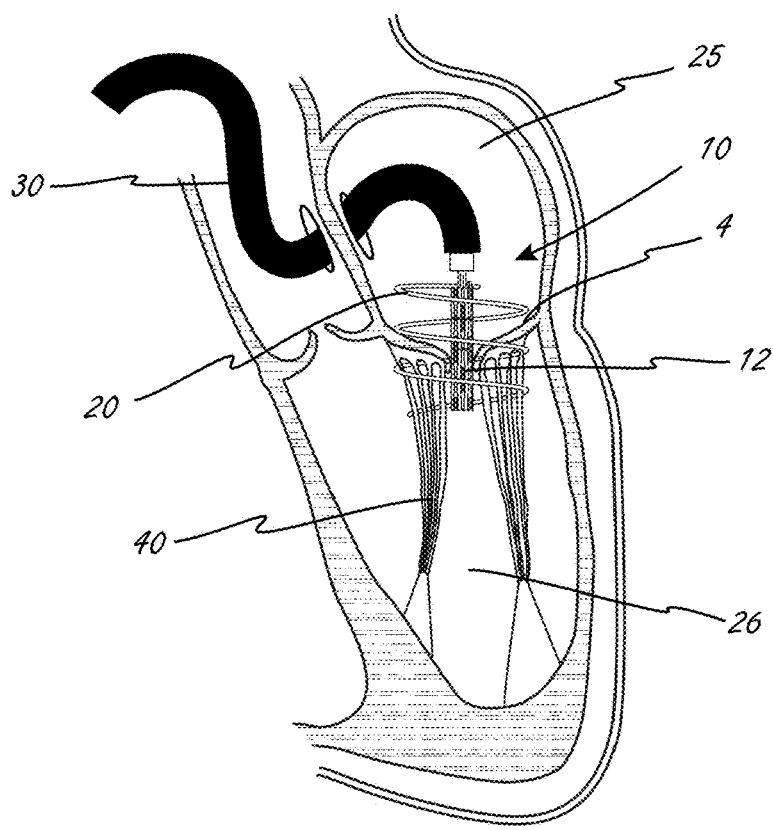
Figure 24:
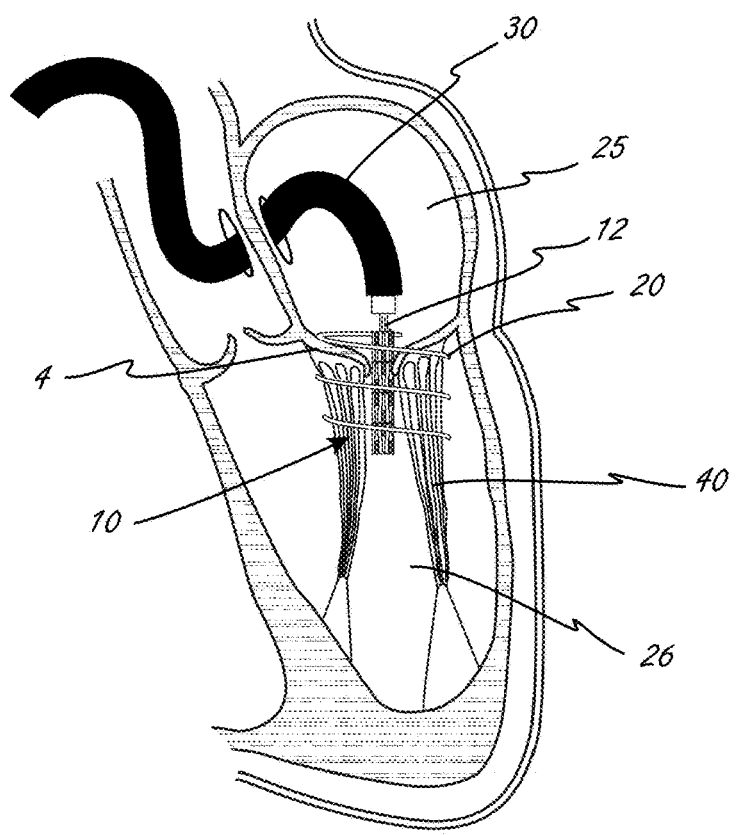

Turning to FIGS. 23-24, valve 10 is anchored to the native valve 4 using exemplary helical wire 20. The valve prosthesis 10—frame 12, wire 20, and valve segment 14—are slowly rotated into the native mitral valve 4. In the illustrated embodiment, a torquer is provided in the delivery catheter 30 for rotating valve 10. Free end 22 of wire 20 is rotated through a commissure and extends below the native valve 4 annulus. The valve prosthesis 4 is further rotated so the free end 22 captures the chordae tendineae (also referred to as "papillary muscles") 40 and/or native valve leaflets 42. As the wire 20 is continually rotated, the chordae tendineae 40 are gathered and pulled radially inward. Free end 22 has a larger radius than the main body of the helical coil in order to facilitate capture of the chordae tendineae 40 during rotation of the valve prosthesis 10. Frame structure 12 also moves into the native valve 4 as the wire 20 is rotated. Valve prosthesis 10 is in the correct position when the chordae tendineae 40 have been captured to a sufficient degree and/or frame structure 12 is in the desired location in the native valve 40. Insertion of the device through the native valve may be facilitated by the natural opening and closing of the native valve during the cardiac cycle. In the illustrated embodiment, the chordae tendineae 40 are pulled inwardly into a bunches (best seen in FIG. 25). The native valve leaflets 42 are also in communication with the helical coil 20. At this stage valve device 10 is rigidly anchored adjacent the native valve 40 annulus.

If the clinician desires to remove or reposition the valve, the helical wire 20 can be counter-rotated to back out the device 10 from the native valve 4. The implant rotation procedure can then be repeated.

Figure 25:
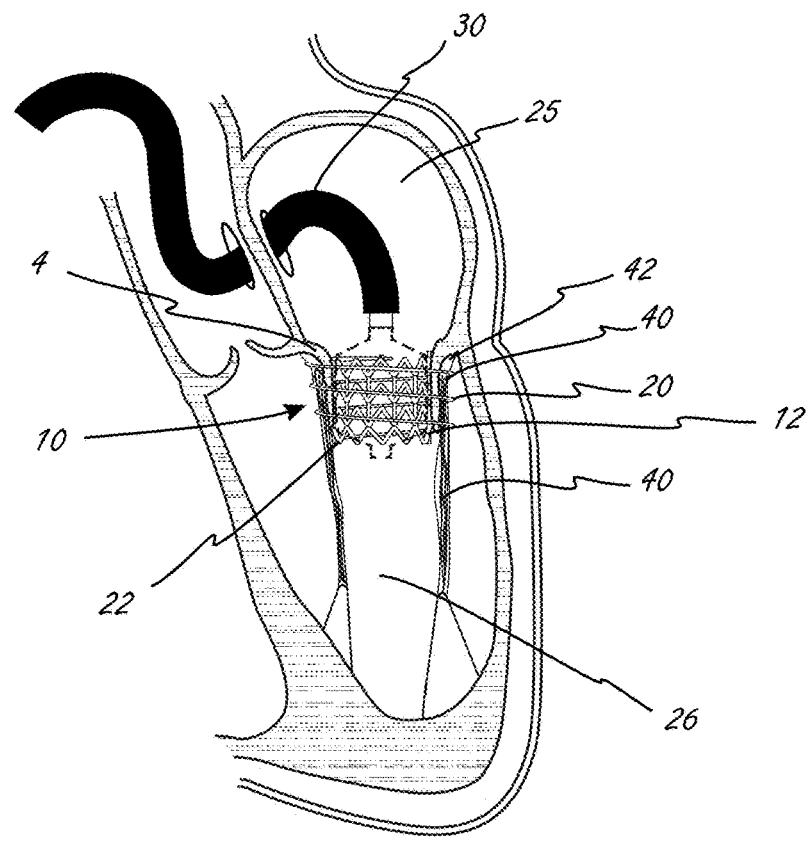
Figure 27:
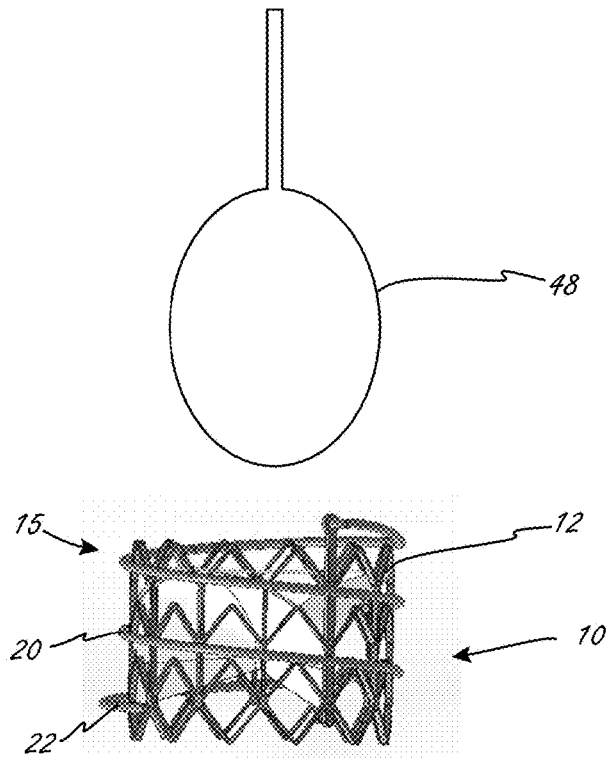
FIGS. 27 to 28 illustrate expanding of the frame structure using a balloon, in accordance with embodiments.
Figure 28:
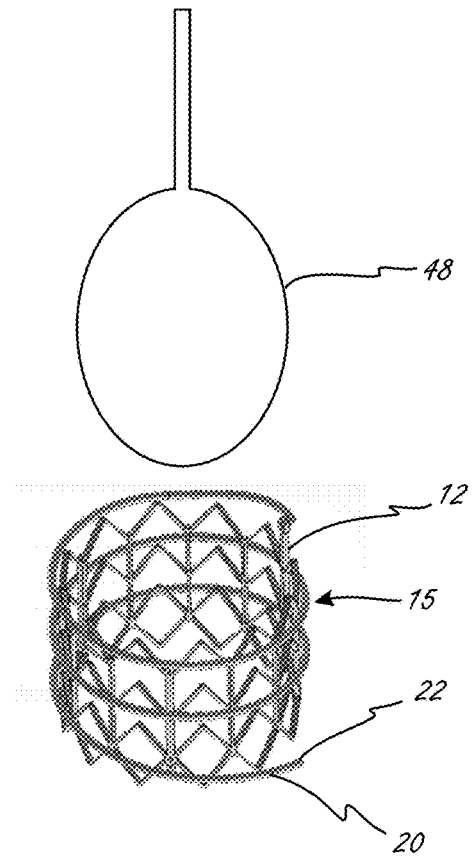

Frame structure 12 is expanded once valve 10 is in the desired location as shown in FIG. 25. The frame structure 12 may comprise a first and second opposite ends, the first end extending above a native valve and the second end extending below the native valve when the frame structure 12 is anchored to the native valve 4. In the illustrated embodiment, the frame structure 12 is expanded with a balloon 48 as shown in FIGS. 27-28. In various embodiments, the frame structure 12 is self-expanding. The self-expanding exemplary frame structure 12 is formed of a shape memory material or any material having superelastic properties. The self-expanding frame structure 12 is configured and expands in a similar manner to a self-expanding stent or scaffold. Expanding the frame structure 12 comprises removing a sheath (for example, outer sheath 50) of the delivery device 30 from the frame structure 12.

Figure 26:
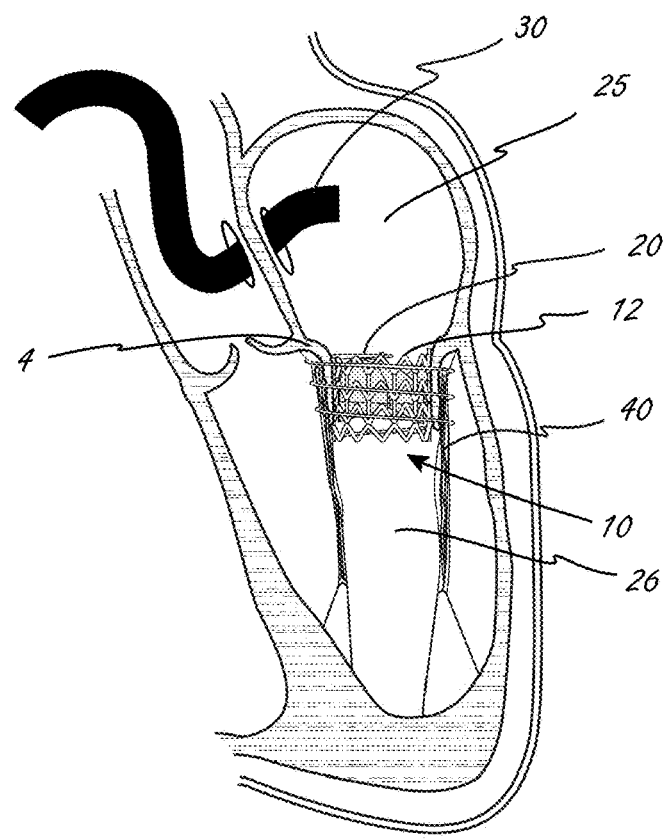

Once the frame structure 12 is expanded the entire valve assembly 10 is released from the delivery catheter 30 and the delivery catheter 30 is removed as shown in FIG. 26. In some embodiments, expansion of the frame structure 12 may occur simultaneously with release of the frame structure 12 from the delivery catheter 30.

In the illustrated embodiment, the valve structure 14 and frame structure 12 are deployed together. One of ordinary skill in the art will appreciate, however, that the frame structure 12 can be deployed first and then receive the prosthetic valve segment 14.

In various embodiments, valve prosthesis 10 does not include a valve segment 14. Instead, the frame structure 12 and anchor 15 are positioned within the native valve 4. The frame structure 12 is configured to receive a valve segment 14 delivered separately. In certain embodiments, the frame structure 12 can be configured to receive one of several valve sizes and types. In this manner, a clinician can choose the proper valve for the individual patient.

In the illustrated embodiment, the helical wire 20 of anchor 15 guides the valve system 10 along a desired axis into position adjacent the native valve 4. The wire 20 also provides an initial anchoring. The valve prosthesis 10 is finally anchored when the frame structure 12 is expanded within the native valve 4. The frame structure 12 dilates the valve leaflets 14 and the compressive force fixes the valve prosthesis 10 into position. Thereafter tissue ingrowth ensures the valve prosthesis 10 remains seated and does not migrate.

The valve device in accordance with the present disclosure provides several advantages over conventional valve systems. Embodiments described herein provide an easy-to-use, repositionable device. Unlike conventional valve systems, the valve prosthesis described herein reduces the risk of injuring or tearing chordae. Typical mitral valve replacement systems involve implanting a prosthetic annulus or ring around the valve. The ring increases the circumference of the valve and risks occluding the entry to the aortic valve. The valve device described herein overcomes these and other problems.

Figure 29:
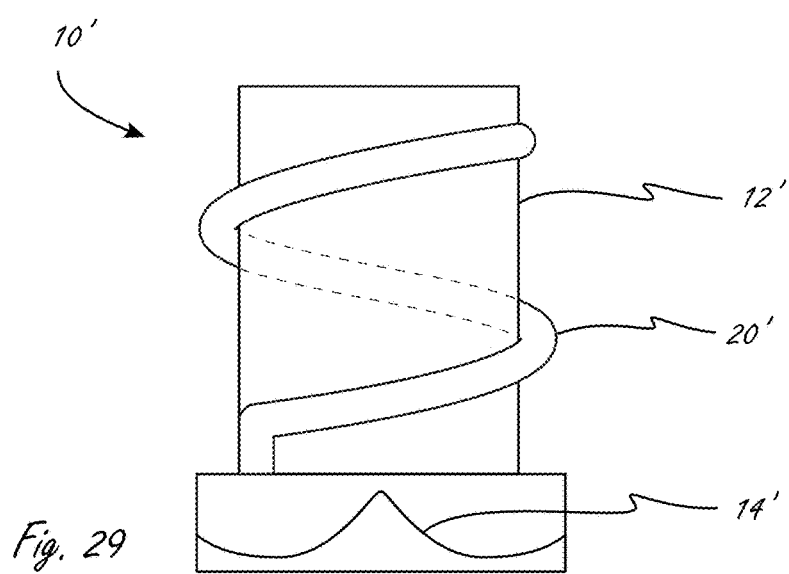
FIG. 29 is a front view of another percutaneous valve similar to the one of FIG. 6, in accordance with embodiments.

FIG. 29 illustrates another embodiment in accordance with the present disclosure. A valve prosthesis 10' includes a helical wire 20' and frame structure 12'. Valve structure 10' is similar to valve 10 except that valve segment 14' is fixed within a separate end of frame structure 12'. Wire 20' is wrapped around a lower portion of the frame structure 12 having a smaller diameter than the upper portion of the frame structure 12 to which the valve segment 14' is fixed.

FIGS. 30A to 30F illustrate several other embodiments in accordance with the present disclosure. Each of valves 10a to 10f includes a helical wire and frame. Each can optionally include a valve segment within the frame.

Figure 30A:
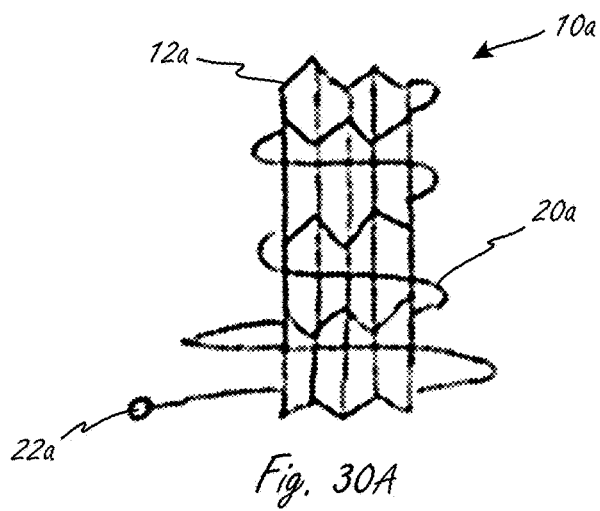
FIGS. 30A to 30F are front views of other percutaneous valves similar to the one of FIG. 6, in accordance with embodiments.

FIG. 30A shows a valve prosthesis 10a which is similar to valve prosthesis 10 except that free end 22a includes an atraumatic ball tip. Also, wire 20a has a tubular shape at one end and a frustoconical shape at another end. Frame structure 12a is substantially similar to frame structure 12.

Figure 30B:
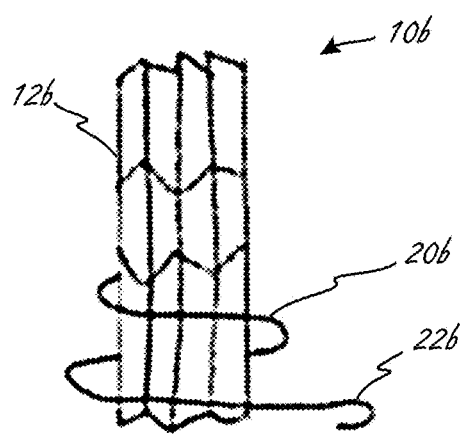

FIG. 30B shows a valve prosthesis 10b which is similar to valve prosthesis 10 except that free end 22 has a pigtail tip. Also, wire 20b is attached to an intermediate portion of frame structure 12b instead of an end of the frame structure 12b. Frame structure 12b is substantially similar to frame structure 12.

Figure 30C:
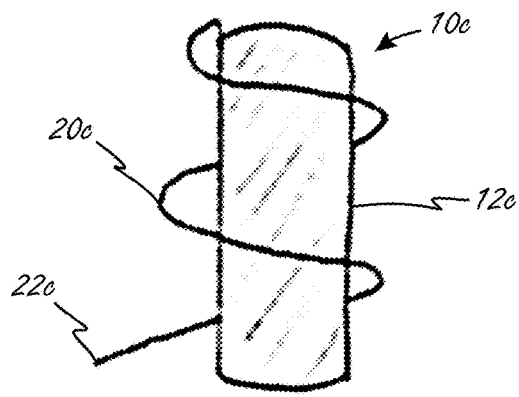

FIG. 30C shows a valve prosthesis 10c which is similar to valve prosthesis 10 except that frame structure 12c is a tubular structure instead of a scaffold or stent-like structure. The frame structure 12c can be formed of expandable materials such as polyurethane or polycarbonate urethane. The wire 20c is substantially similar to wire 20. The free end 22c is substantially similar to free end 22.

Figure 30D:
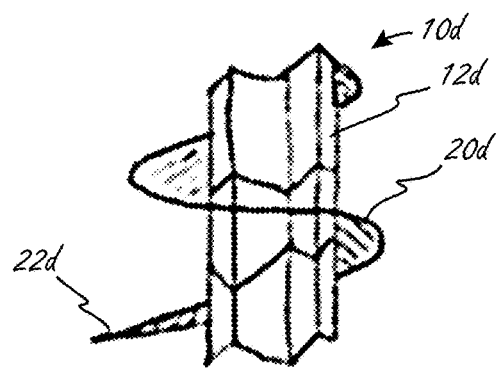

FIG. 30D shows a valve prosthesis 10d which is similar to valve prosthesis 10 except that the anchor 15 is formed of a three-dimensional surface 20d instead of a wire 20. Three-dimensional surface 20d comprises a free end 22d, which may be substantially similar to any of the free ends described herein. Frame structure 12d is substantially similar to frame structure 12.

Figure 30E:
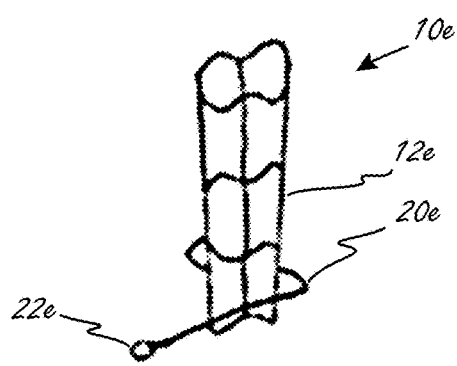

FIG. 30E shows a valve prosthesis 10e which is similar to valve prosthesis 10 except that frame structure 12e has a conical shape instead of a tubular shape. One will appreciate from the description herein that the frame structure 12 may take a variety of shapes in accordance with the present disclosure. The wire 20e is substantially similar to wire 20. The free end 22e is substantially similar to free end 22.

Figure 30F:
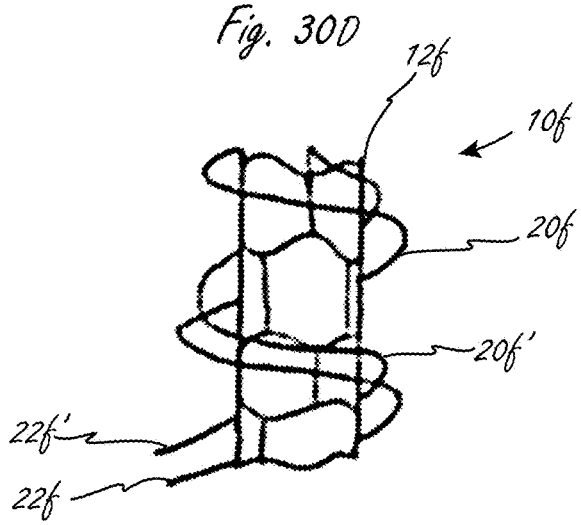

FIG. 30F shows a valve prosthesis 10f which is similar to valve prosthesis 10 except that the valve device 10f includes a plurality of wires 20f and 20f'. The use of a plurality of wires 20f and 20f' provides increased anchoring security. Because it may be difficult to insert both free ends 22f and 22f', one or both free ends 22f and 22f' may include a sharp point for piercing tissue. In this manner, the sharp end can pierce the valve annulus or leaflets. Barbs or other mechanisms may be employed to increase anchoring of the wire.

For example, one or both of the wires 20f and 20f' may include a braided surface or barbs to prevent axial dislocation once it is screwed into place.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The foregoing descriptions of specific embodiments of the present invention have been presented for purposes of illustration and description. They are not intended to be exhaustive or to limit the invention to the precise forms disclosed, and obviously many modifications, changes, substitutions, alternatives, and variations are possible in light of the above teaching. The embodiments were chosen and described to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A heart valve prosthesis for replacing a diseased native valve in a heart of a patient, the valve prosthesis comprising:
a compressible and expandable frame structure having a frame axis;
a valve segment disposed within the frame structure, the valve segment comprising a biocompatible one-way valve; and
a compressible and expandable anchor permanently attached to and configured to encircle an outer periphery of the frame structure, wherein the anchor comprises a spiral wire and a free end, the free end having a larger radius of curvature than the spiral wire;
wherein the heart valve prosthesis has an anchoring configuration in which the anchor is in an expanded state, the frame structure is in a collapsed state, and the frame axis is centrally located within the spiral wire;
wherein when heart valve prosthesis is in the anchoring configuration, rotation of the spiral wire is configured to guide the frame structure into the native valve.

2. The valve prosthesis of claim 1, wherein the free end is configured to guide the spiral wire through a commissure of a native valve of a patient.

3. The valve prosthesis of claim 1, wherein the free end comprises an atraumatic tip.

4. The valve prosthesis of claim 3, wherein the free end comprises a ball tip.

5. The valve prosthesis of claim 1, wherein the free end is configured for piercing tissue.

6. The valve prosthesis of claim 1, wherein the frame structure is configured for expanding within a native valve of a patient.

7. The valve prosthesis of claim 1, wherein the frame structure has a compressed state sized and dimensioned for percutaneous insertion and an expanded state sized and dimensioned for implantation in a native valve of a patient.

8. The valve prosthesis of claim 1, wherein the frame structure comprises first and second opposite ends, the first end configured to extend above a native valve and the second end configured to extend below the native valve when the valve prosthesis is positioned across the native valve.

9. The valve prosthesis of claim 1, wherein the frame structure comprises an expandable stent.

10. The valve prosthesis of claim 1, wherein the frame structure comprises a generally tubular expanded shape.

11. The valve prosthesis of claim 1, wherein the frame structure comprises an expanded outer periphery and a compressed outer periphery when subject to an external radial force, wherein the compressed outer periphery is smaller in diameter than the expanded outer periphery.

12. The valve prosthesis of claim 1, wherein the frame structure is self-expanding.

13. The valve prosthesis of claim 1, wherein the valve segment comprises at least one leaflet having an inner layer and an outer layer, and wherein the frame structure is attached to the outer layer at one or more ends of the frame structure.

14. The valve prosthesis of claim 1, wherein the valve segment comprises a plurality of leaflets.

15. The valve prosthesis of claim 14, wherein the valve segment comprises two leaflets.

16. The valve prosthesis of claim 1, wherein the anchor and the frame structure are adapted to be independently and separately expanded.

17. The valve prosthesis of claim 1, wherein the spiral wire is fixedly connected to the frame structure only at one end of the spiral wire.

18. The valve prosthesis of claim 1, wherein the free end is configured to capture chordae tendineae of the native valve when the anchor is rotated within the heart in the anchoring configuration.

19. The valve prosthesis of claim 1, wherein in the anchoring configuration, the frame axis is aligned with a central axis of the anchor.

20. The valve prosthesis of claim 1, wherein the anchor is configured to concentrically encircle the outer periphery of the frame structure.

* * * * *